US008518885B2

(12) United States Patent
Powers et al.

(10) Patent No.: US 8,518,885 B2
(45) Date of Patent: Aug. 27, 2013

(54) HETEROCYCLIC PEPTIDE KETOAMIDES

(75) Inventors: James C. Powers, Atlanta, GA (US);
Jonathan D. Glass, Atlanta, GA (US);
Asli Ovat, Smyrna, GA (US); Zhaozhao Li, Alpharetta, GA (US)

(73) Assignees: Georgia Tech Research Corporation, Atlanta, GA (US); Emory University, Atlanta, GA (US)

( * ) Notice: Subject to any disclaimer, the term of this patent is extended or adjusted under 35 U.S.C. 154(b) by 99 days.

(21) Appl. No.: 12/866,541

(22) PCT Filed: Jul. 16, 2008

(86) PCT No.: PCT/US2008/008650
§ 371 (c)(1),
(2), (4) Date: Nov. 15, 2010

(87) PCT Pub. No.: WO2009/099416
PCT Pub. Date: Aug. 13, 2009

(65) Prior Publication Data
US 2011/0053858 A1 Mar. 3, 2011

Related U.S. Application Data

(60) Provisional application No. 61/026,583, filed on Feb. 6, 2008.

(51) Int. Cl.
*A61K 38/05* (2006.01)
*C07K 5/06* (2006.01)

(52) U.S. Cl.
USPC ........ 514/17.7; 514/17.8; 514/17.9; 514/18.2; 514/20.2; 514/21.91; 544/265; 544/277; 544/316; 544/317; 544/329; 544/335; 564/153

(58) Field of Classification Search
None
See application file for complete search history.

(56) References Cited

U.S. PATENT DOCUMENTS

| | | | |
|---|---|---|---|
| 5,514,694 A | 5/1996 | Powers et al. | |
| 5,610,297 A | 3/1997 | Powers | |
| 5,650,508 A | 7/1997 | Powers | |
| 5,763,576 A | 6/1998 | Powers | |
| 6,235,929 B1 | 5/2001 | Powers | |
| 6,288,231 B1 | 9/2001 | Chatterjee et al. | |

FOREIGN PATENT DOCUMENTS

WO  WO 2004/028466 A2  4/2004

OTHER PUBLICATIONS

Barrett et al., "Novel, potent $P^2$-$P^3$ pyrrolidine derivatives of ketoamide-based cathepsin K inhibitors," *Bioorg. Med. Chem. Lett.* 16:1735-1739 (2006).
Barrett et al., "$P^2$-$P^3$ conformationally constrained ketoamide-based inhibitors of cathepsin K," *Bioorg. Med. Chem. Lett.* 15:3540-3546 (2005).
Barrett et al., "A structural screening approach to ketoamide-based inhibitors of cathepsin K," *Bioorg. Med. Chem. Lett.* 15:2209-2213 (2005).
Barrett et al., "Potent and selective $P^2$-$P^3$ ketoamide inhibitors of cathepsin K with good pharmacokinetic properties via favorable $P^{1'}$, $P^1$, and/or $P^3$ substitutions," *Bioorg. Med. Chem. Lett.* 14:4897-4902 (2004).
Barrett et al., "Orally bioavailable small molecule ketoamide-based inhibitors of cathepsin K," *Bioorg. Med. Chem. Lett.*, 14:2543-2546 (2004).
Barrett et al., "Cathepsin B, Cathepsin H, and Cathepsin L," *Methods Enzymol.*, 80:535-561 (1981).
Bartus, "The calpain hypothesis of neurodegeneration: evidence for a common cytotoxic pathway," *Neuroscientist*, 3(5):314-327 (1997).
Bihovsky et al., "1,2-Benzothiazine 1,1-dioxide α-ketoamide analogues as potent calpain I inhibitors" *Bioorg. Med. Chem. Lett.*, 14:1035-1038 (2004).
Catalano et al., "Design of small molecule ketoamide-based inhibitors of cathepsin K," *Bioorg. Med. Chem. Lett.*, 14:719-722 (2004).
Charles et al., "Bicyclic Heterocycles with nitrogen at the Ring Junction. Part 2. Application of the Dakin-West Reaction to the Synthesis of Imidazo-[5,1-$f$]-1,2,4-triazin-4(3$H$)-ones," *J. Chem. Soc. Perkin 1*, 1139-1146 (1980).
Chatterjee et al. "$P_2$-achiral, P'-extended α-ketoamide inhibitors of Calpain I," *Bioorg. Med. Chem. Lett.*, 9:2371-2374 (1999).
Chu et al., "Peptide α-Oxo Esters, α-Oxo Acids, and α-Oxoamides," *Methods of Organic Chemistry*, E22d:244-255 (2003).
Cuerrier et al., "Calpain inhibition by α-ketoamide and cyclic hemiacetel inhibitors revealed by X-ray crystallography," *Biochemistry*, 45(24):7446-7452 (2006).
Donkor et al., "Design, synthesis, molecular modeling studies, and calpain inhibitory activity of novel alpha-ketoamides incorporating polar residues at the $P_1$'-position," *J. Med. Chem.*, 47:72-79 (2004).
Donkor, "A survey of calpain inhibitors," *Curr. Med. Chem.*, 7:1171-1188 (2000).
Donkor et al., "Synthesis and calpain inhibitory activity of α-ketoamides with 2,3-methanoleucine stereoisomers at the $P_2$ position," *Bioorg. Med. Chem. Lett.*, 10:2497-2500 (2000).
Hou et al., "Efficient syntheses of oncinotine and neooncinotine," *J. Org. Chem.*, 69(18):6094-6099 (2004).
Huang et al., "Ester and amide derivatives of E64c as inhibitors of platelet calpains," *J. Med. Chem.*, 35:2048-2054 (1992).
Kanaoka et al., "Synthesis of a key fluorogenic amide, $L$-arginine-4-methycoumaryl-7-aide ($L$ -arg-MCA) and its derivatives. Fluorescence assays for trypsin and papain," *Chem. Pharm. Bull.*, 25:3126-3128 (1977).

(Continued)

*Primary Examiner* — Jeffrey E Russel
(74) *Attorney, Agent, or Firm* — Meunier Carlin & Curfman, LLC

(57) ABSTRACT

A novel class of peptide α-ketoamides useful for selectively inhibiting calpains, selectively inhibiting cysteine proteases, and generally inhibiting all cysteine proteases, having the formula $M-AA^2-AA^1-CO-NH-(CH_2)_n-R^3$. Processes for the synthesis of peptidyl α-ketoamide derivatives. Compositions and methods for inhibiting cysteine proteases, inhibiting calpains, and treating disease caused by cysteine proteases and calpains are provided.

24 Claims, 2 Drawing Sheets

(56) References Cited

OTHER PUBLICATIONS

Kitahara et al., "Large-scale purification of porcine calpain I and calpain II and comparison of proteolytic fragments of their subunits," *J. Biochem.*, 95(6):1759-1766 (1984).

Korukonda et al., "Synthesis, calpin inhibitory activity, and cytotoxicity of $P_2$-substituted proline and thiaproline peptidyl aldehydes and peptidyl α-ketoamides," *J. Med. Chem.* 49:5282-5290 (2006).

Krauser et al., "Calpain," *In Proteinase and Peptidase Inhibition: Recent Potential Targets for Drug Development*, Smith and Simons, Eds., Taylor & Francis, New York, 6:127-153 (2000).

Lafitte et al., "Quadruply hydrogen bonded cytosine modules for supramolecular applications," *J. Am. Chem. Soc.*, 128(20):6544-6545 (2006).

Lee et al., "Synthesis and biological evaluation of chromone carboxamides as calpain inhibitors," *Bioorg. Med. Chem. Lett.*, 15:2857-2860 (2005).

Lescop et al., "Novel cell-penetrating a-keto-amide calpain inhibitors as potential treatment for muscular dystrophy," *Bioorg. Med. Chem. Lett.*, 15:5176-5181 (2005).

Li et al., "Novel peptidyl α-ketoamide inhibitors of calpains and other cysteine proteases," *J. Med. Chem.*, 39:4089-4098 (1996).

Li et al., "Peptide α-keto ester, α-keto amide and α-keto acid inhibitors of calpains and other cysteine proteases," *J. Med. Chem.*, 36:3472-3480 (1993).

Lubisch et al., "Benzoylalanine-derived ketoamides carrying vinylbenzyl amino residues: discovery of potent water-soluble calpain inhibitors with oral bioavailability," *J. Med. Chem.*, 46:2404-2412 (2003).

Lubisch et al., "Discovery of phenyl alanine derived ketoamides carrying benzoyl residues as novel calpain inhibitors," *Bioorg. Med. Chem. Lett.*, 12:1335-1338 (2002).

Nowick et al., "An improved method for the synthesis of enantiomerically pure amino acid ester isocyanates," *J. Org. Chem.* 57:7364-7366 (1992).

Powers et al., "Irreversible inhibitors of serine, cysteine, and threonine proteases," *Chem. Rev.*, 102:4639-4750 (2002).

Powers, "Calpain Inhibitors," *In Design of Enzyme Inhibitors as Drugs*, Sandler and Smith, Eds., Oxford University Press, Oxford, 2:754-766 (1994).

Rich, "Inhibitors of cysteine proteinases," *In Protease Inhibitors*, Barrett and Salvesen, Eds., Elsevier, New York, 4:153-178 (1986).

Sasaki et al., "Comparative specificity and kinetic studies on porcine calpain I and calpain II with naturally occurring peptides and synthetic fluorogenic substrates," *J. Biol. Chem.*, 259:12489-12494 (1984).

Shirasaki et al., "Exploration of orally available calpain inhibitors. Part 3: Dipeptidyl α-ketoamide derivatives containing pyridine moiety," *Bioorg. Med. Chem.*, 14:5691-5698 (2006).

Shirasaki et al., "Exploration of orally available calpain inhibitors: peptidyl α-ketoamides containing an amphiphile at P3 site," *Bioorg. Med. Chem.*, 13:4473-4484 (2005).

Siman et al., "Brain Fodrin: Substrate for Calpain I, an Endogenous Calcium-Activated Protease," *Proc. Natl. Acad. Sci. USA*, 81:3572-3576 (1984).

Summers et al., "Synthesis of fluorescent labeled derivatives of aminopropylpyrimidines," *J. Org. Chem.*, 40(11):1559-1561 (1975).

Tavares et al., "Potent and selective ketoamide-based inhibitors of cysteine protease, cathepsin K," *J. Med. Chem.*, 47:5049-5056 (2004).

Tavares et al., "Ketoamide-based inhibitors of cysteine protease, cathepsin K: P3 modifications," *J. Med. Chem.*, 47:5057-5068 (2004).

Tsujinaka et al., "Synthesis of a new cell-penetrating calpain inhibitor (calpeptin)," *Biochem. Biophys. Res. Commun.*, 153(3):1201-1208 (1988).

Weyermann et al. "Synthesis and evaluation of calpain inhibitors carrying muscle cell targeting groups," *Lett. Drug Design & Discovery*, 3:152-158 (2006).

Zhang et al., "Syntheses and coordination chemistry of aminomethylphosphine derivatives of adenine," *Euro. J. Inorg. Chem.*, 13:2426-2437 (2003).

Extended European Search Report, Aug. 10, 2011.

Ovat et al., "Peptidyl α-Ketoamides with Nucleobases, Methylpiperazine, and Dimethylaminoalkyl Substituents as Calpain Inhibitors" J. Med. Chem., 53:6326-6336 (2010).

Qian et al., "Cocrystal Structures of Primed Side-Extending a-Ketoamide Inhibitors Reveal Novel Calpain-Inhibitor Aromatic Interactions" J. Med. Chem., 51:5264-5270 (2008).

US 8,518,885 B2

HETEROCYCLIC PEPTIDE KETOAMIDES

CROSS REFERENCE TO RELATED APPLICATIONS

This application claims priority to U.S. Provisional Application No. 61/026,583, filed Feb. 6, 2008, herein incorporated by reference in its entirety.

STATEMENT REGARDING FEDERALLY SPONSORED RESEARCH

This invention was made with government support under Grant No. 1 R21NS053801 awarded by Public Health Services, National Institutes of Health. The U.S. Government has certain rights in this invention.

REFERENCE TO SEQUENCE LISTING

The Sequence Listing submitted Jun. 11, 2013, as a text file named "10034_009US1_2013_06_11_Sequence_Listing.txt," created on Jun. 11, 2013, and having a size of 1 KB is hereby incorporated by reference pursuant to 37 C.F.R. §1.52(e)(5).

FIELD

The disclosed subject matter generally relates to peptide ketoamide cysteine protease inhibitors. Other aspects of the disclosed subject matter relate to methods of using the disclosed compositions for inhibiting cysteine proteases such as calpain, as well as other cysteine proteases, and for the treatment of various diseases.

BACKGROUND

Cysteine proteases such as calpain use a cysteine residue in their catalytic mechanism in contrast to serine proteases which utilize a serine residue. Cysteine proteases include papain, cathepsin B, calpains, and several viral and parasite enzymes. Neural tissues, including brain, are known to possess a large variety of proteases, including at least two calcium stimulated proteases termed calpains. Calpains are ubiquitous cytosolic proteolytic enzymes involved in both physiological and pathological cellular functions. Limited activation of calpains results in modification or activation of protein receptors, enzymes, and cytoskeletal proteins. Pathological cellular insults lead to more generalized calpain activation, resulting in cytoskeletal degradation and cell death. Calpain activation likely occurs due to sustained elevation of intracellular calcium that is a common feature of models of neuronal injury (Bartus, "The calpain hypothesis of neurodegeneration: evidence for a common cytotoxic pathway," *Neuroscientist* 3:314-27, 1997, which is incorporated by reference herein in its entirety).

While calpains degrade a wide variety of protein substrates, cytoskeletal proteins seem to be particularly susceptible to attack. In some cases, the products of the proteolytic digestion of these proteins by calpain are distinctive and persistent over time. Since cytoskeletal proteins are major components of certain types of cells, this provides a simple method of detecting calpain activity in cells and tissues. Thus, calpain activation can be measured indirectly by assaying the proteolysis of the cytoskeletal protein spectrin, which produces a large, distinctive and biologically persistent breakdown product when attacked by calpain (Siman et al., *Proc. Natl. Acad. Sci. USA* 81:3572-76, 1984, which is incorporated by reference herein in its entirety). Activation of calpains and/or accumulation of breakdown products of cytoskeletal elements have been observed in neural tissues of mammals exposed to a wide variety of neurodegenerative diseases and conditions. For example, these phenomena have been observed following ischemia in gerbils and rats, following stroke in humans, following administration of the toxins kainate, trimethyltin or colchicine in rats, and in human Alzheimer's disease. In the nervous system, calpain activation is believed to be responsible for the calcium-mediated cell injury seen in ischemic stroke, spinal cord injury, closed head injury, Wallerian degeneration, ALS, and peripheral neuropathy.

Calpains are present, in many tissues in addition to the brain. Calpain I is activated by micromolar concentrations of calcium while calpain II is activated by millimolar concentrations. In the brain, calpain II is the predominant form, but calpain I is found at synaptic endings and is thought to be the form involved in long term potentiation, synaptic plasticity, and cell death. Other $Ca^{2+}$ activated cysteine proteases may exist, and the term "calpain" is used to refer to all $Ca^{2+}$ activated cysteine proteases, including calpain I and calpain II. The terms "calpain I" and "calpain II" are used herein to refer to the micromolar and millimolar activated calpains, respectively, as described above.

Cathepsin B, cathepsin L, cathepsin S, and other cathepsins are involved in muscular dystrophy, myocardial tissue damage, tumor metastasis, and bone resorption. In addition, a number of viral processing enzymes, which are essential for viral infection, are cysteine proteases. Inhibitors of cysteine proteases would thus have multiple therapeutic uses.

Numerous inhibitors of calpain and other cysteine protease have been described in the literature. These include peptide aldehydes such as Ac-Leu-Leu-Nle-H and leupeptin (Ac-Leu-Leu-Arg-H), as well as epoxysuccinates such as E-64. These compounds are not especially useful at inhibiting calpain in neural tissue in vivo because they are poorly membrane permeant and, accordingly, are not likely to cross the blood brain barrier very well. Also, many of these inhibitors have poor specificity and will inhibit a wide variety of proteases in addition to calpain. In addition, other classes of compounds that inhibit cysteine proteases include peptide diazomethyl ketones (Rich, In Protease Inhibitors, Barrett and Salvesen, Eds., Elsevier, N.Y., 1986, pp 153-78, which is incorporated by reference herein).

Potent calpain inhibitors are in general either transition-state analogs or irreversible covalent inhibitors. The active site of a cysteine protease contains Cys and His residue along with the so-called oxyanion hole. The mechanism of substrate hydrolysis involves the attack of the active site Cys on the scissile peptide bond. The active site cysteine of the enzyme adds to the scissile amide carbonyl group to form a tetrahedral adduct forming an oxyanion that interacts with the so called oxyanion hole. Subsequently, the tetrahedral adduct forms an acyl enzyme intermediate, which is then cleaved to the two hydrolysis products. Transition-state analog inhibitors such as peptide aldehydes, ketones, and α-ketoamides reversibly inhibit cysteine proteases by forming a hemithioacetal through reaction with the active site cysteine thiol group. This resembles the tetrahedral transition state involved in normal peptide substrate hydrolysis. Transition state inhibitors are very potent reversible inhibitors for cysteine proteases, since the enzyme has evolved to bind the tetrahedral transition state effectively.

Additional references to calpain inhibitors in the literatures are Tsujinaka et al., "Synthesis of a new cell-penetrating calpain inhibitor (calpeptin)," *Biochem. Biophys. Res. Com-* mun. 153:1201-08, 1988; Huang et al., "Amide derivatives of E64c as inhibitors of platelet calpains," *J. Med. Chem.* 35:2048-54, 1992; Powers et al., "Irreversible inhibitors of serine, cysteine, and threonine proteases," *Chem. Rev.* 102: 4639-750, 2002; Powers, "Calpain Inhibitors," In Design of Enzyme Inhibitors as Drugs," Sandler and Smith, Eds., Oxford University Press, Oxford, 1994; Vol. 2, pp 754-66; Donkor, "A survey of calpain inhibitors," *Curr. Med. Chem.* 7:1171-88, 2000; Krauser and Powers, "Calpain," In Proteinase and Peptidase Inhibition: Recent Potential Targets for Drug Development, Smith and Simons, Eds., Taylor & Francis, New York, 2000, pp. 127-53, each of which are incorporated by reference herein in their entireties.

Dipeptidyl and tripeptidyl α-ketoesters, α-ketoamides and α-ketoacid transition-state inhibitors of calpains I and II have been reported in the literature. See for example Li et al., "Novel peptidyl α-ketoamide inhibitors of calpains and other cysteine proteases," *J. Med. Chem.* 39:4089-98, 1996; Li et al., "Peptide α-ketoester, α-ketoamide and α-ketoacid inhibitors of calpains and other cysteine proteases," *J. Med. Chem.* 36:3472-80, 1993, each of which are incorporated herein by reference in their entities. The composition in these publications are also disclosed in several patents: U.S. Pat. No. 5,514,694, issued May 7, 1996, to Powers et al.; U.S. Pat. No. 5,610,297, issued Mar. 11, 1997, to Powers; U.S. Pat. No. 5,650,508, issued Jul. 22, 1997, to Powers; U.S. Pat. No. 5,763,576, issued Jun. 9, 1998, to Powers; and U.S. Pat. No. 6,235,929, issued May 22, 2001, to Powers, each of which are incorporated herein by reference in their entireties.

One of the ketoamides, AK295, is a potent transition-state inhibitor for calpain I and II, but does have some inhibitory activity toward other cysteine proteases such as cathepsins (Li et al., *J. Med. Chem.* 36:3472-80, 1993). The ketone carbonyl group of AK295 is the group which forms the hemithioacetal with the active site cysteine of calpain. Since the enzyme has evolved to bind the tetrahedral transition state effectively, transition state inhibitors are usually potent reversible inhibitors for cysteine proteases. Reversibility occurs when the hemiacetal breaks down to reform the carbonyl compound and free enzyme.

No effective therapy has yet been developed for most neurodegenerative diseases and conditions, and other disease related to uncontrolled cysteine protease action. Millions of individuals suffer from neurodegenerative diseases, and thus there is a need for therapies effective in treating and preventing these diseases and conditions. There is a need for new compositions to treat other diseases related to cysteine protease activity. Further, because neuronal pathologies have a dramatic impact on quality of life of patients, there is a need for compositions and methods for treating these disorders, in particular, compositions and methods for treating pathologies with little or reduced side effects such as neuropathy. Thus, there is also a need for compositions and methods of treating other pathologies related to calpain activation. There is still another need for methods and compositions for disease resulting from other cysteine proteases particularly parasitic diseases. The compositions and methods disclosed herein address these and other needs.

SUMMARY

In accordance with the purposes of the disclosed materials, compounds, compositions, and methods, as embodied and broadly described herein, the disclosed subject matter, in one aspect, relates to compositions and methods for preparing and using such compositions. In a further aspect, the disclosed subject matter relates to compositions containing calpain inhibitors, such as peptide α-ketoamides, and methods of their use in inhibiting cysteine protease activity, for inhibiting calpain activity, and for the treatment of a pathology, for example neurodegenerative disease, axonal degeneration, or calcium-induced cell injury, or parasitic diseases.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURE

The accompanying FIGURE, which is incorporated in and constitute a part of this specification, illustrates several aspects described below.

DETAILED DESCRIPTION

Figure 1A:
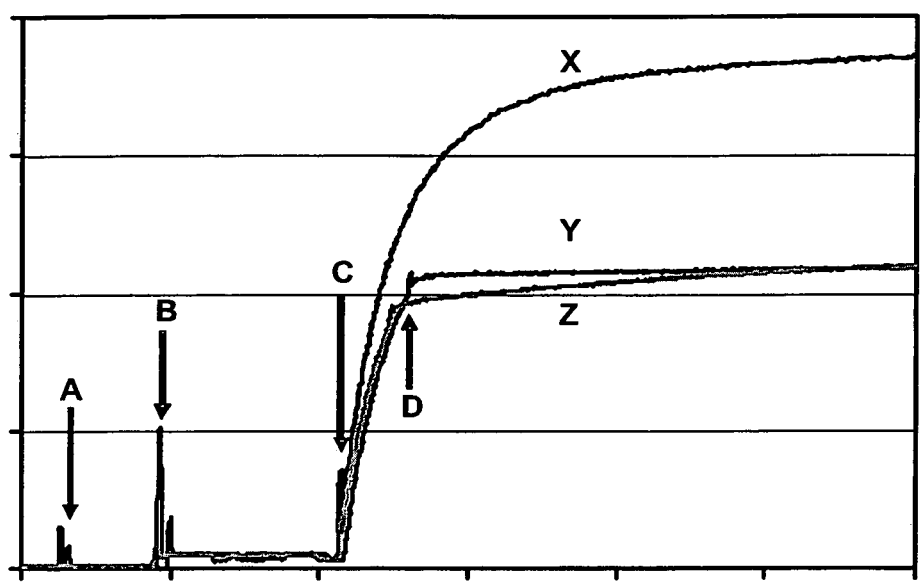
FIG. 1 is a pair of graphs showing the inhibitory effect of Z-Leu-Abu-CONH—$(CH_2)_3$-adenin-9-yl, and Z-Leu-Abu-CONH—$(CH_2)_3$-(4-methylpiperazin-1-yl) on m-calpain (FIG. 1A) and µI-II (FIG. 1B). Duplicate assays were performed by adding 1.3 µM (EDANS)-EPLFAERK(SEQ ID NO:1)-(DABCYL) (A), 125 nM calpain (B), and 4 mM $CaCl_2$ (C), then averaged to yield the plots shown. Autolytic inactivation of m-calpain, but not µI-II, was observed when no inhibitor was added (X). Immediately following addition of each inhibitor (D), the increase in fluorescence intensity was attenuated. Z-Leu-Abu-CONH—$(CH_2)_3$-adenin-9-yl (Y), caused a more distinct attenuation of fluorescence in both the m-calpain and µI-II assays, indicating that it is a more potent inhibitor when compared to Z-Leu-Abu-CONH—$(CH_2)_3$-(4-methylpiperazin-1-yl) (Z).

The materials, compounds, compositions, and methods described herein may be understood more readily by reference to the following detailed description of specific aspects of the disclosed subject matter, the Figures, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Further, disclosed herein are materials, compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a compound is disclosed and a number of modifications that can be made to a number of components or residues of the compound are discussed, each and every combination and permutation that are possible are specifically contemplated unless specifically indicated to the contrary. Thus, if a class of components A, B, and C are disclosed as well as a class of components D, E, and F and an example of a combination composition A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

DEFINITIONS

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a compound" includes mixtures of two or more such compounds, reference to "an agent" includes mixtures of two or more such agents, reference to "the composition" includes mixtures of two or more such compositions, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that these data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

References in the specification and concluding claims to parts by weight of a particular component in a composition denotes the weight relationship between the component and any other components in the composition for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

"Subject," as used herein, means an individual. In one aspect, the subject is a mammal such as a primate, and, in another aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

By the term "effective amount" of a compound or composition as provided herein is meant a nontoxic but sufficient amount of the compound to provide the desired utility, for example to reduce, inhibit, prevent, or heal neuronal injury. As will be pointed out below, the exact amount required will vary from subject to subject, depending on the species, age, body weight, general health, sex, diet, and general condition of the subject, the severity of the condition or disease that is being treated, the particular compound used, its mode of administration, the duration of the treatment; drugs used in combination or coincidental with the specific composition employed, and like factors well known in the medical arts. Thus, it is not possible to specify an exact "effective amount"; however, an appropriate effective amount can be determined by one of ordinary skill in the art using only routine experimentation. For example, it is well within the skill of the art to start doses of a composition at levels lower than those required to achieve the desired therapeutic effect and to gradually increase the dosage until the desired effect is achieved. One can also evaluate the particular aspects of the medical history, signs, symptoms, and objective laboratory tests that are known to be useful in evaluating the status of a subject in need of attention for the treatment of a disease. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: 1) a subject's physical condition is shown to be improved, 2) the progression of the disease or condition is shown to be stabilized, or slowed, or reversed, or 3) the need for other medications for treating the disease or condition is lessened or obviated, then a particular treatment regimen will be considered efficacious. If desired, the effective daily dose can be divided into multiple doses for purposes of administration. Consequently, single dose compositions can contain such amounts or submultiples thereof to make up the daily dose. The dosage can be adjusted by the individual physician or the subject in the event of any counterindications. Dosage can vary, and can be administered in one or more dose administrations daily, for one or several days. Guidance can be found in the literature for appropriate dosages for given classes of pharmaceutical products.

The terms "higher," "increases," "elevates," or "enhanced" refer to increases above basal levels, e.g., as compared to a control. The terms "lower," "decreases," "reduces," or "reduction" refer to decreases below basal levels, e.g., as compared to a control. By "control" is meant either a subject, organ, tissue, or cell lacking a disease or injury, or a subject, organ, tissue, or cell in the absence of a particular variable such as a therapeutic agent. A subject, organ, tissue, or cell in the absence of a therapeutic agent can be the same subject, organ, tissue, or cell before or after treatment with a therapeutic agent or can be a different subject, organ, tissue, or cell in the absence of the therapeutic agent. Comparison to a control can include a comparison to a known control level or value known in the art. Thus, basal levels are normal in vivo levels prior to, or in the absence of, the addition of an agent (e.g., a therapeutic agent) or another molecule. The term "modulate" is used herein to refer to an increase or decrease, as defined herein.

The term "pharmaceutically acceptable" means a material that is not biologically or otherwise undesirable, i.e., the material can be administered to an individual along with the selected bicyclic compound without causing any undesirable biological effects or interacting in a deleterious manner with any of the other components of the pharmaceutical composition in which it is contained.

The term "pharmaceutically acceptable salt(s)," unless otherwise indicated, includes salts of acidic or basic groups that may be present in the compounds of Formula I.

The compounds of Formula I that are basic in nature are capable of forming a wide variety of salts with various inorganic and organic acids. The acids that may be used to prepare pharmaceutically acceptable acid addition salts of such basic compounds of Formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, TFA, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Those compounds of the Formula I that are acidic in nature are capable of forming base salts with various pharmacologically acceptable cations. Examples of such salts include the alkali metal or alkaline earth metal salts and particularly, the sodium and potassium salts.

The term "pharmaceutically acceptable derivative" refers to any homolog, analog, or fragment corresponding to the peptide ketoamides disclosed herein, which inhibits protease activity and is relatively non-toxic to the subject or host.

As used herein, and without limitation, the term "derivative" is used to refer to any compound which has a structure derived from the structure of the compounds disclosed herein and whose structure is sufficiently similar to those disclosed herein and based upon that similarity, would be expected, by one skilled in the art, to exhibit the same or similar activities and utilities as the claimed compounds.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more (e.g., referred to as "disubstitued," "trisubstituted," and the like) and the same or different for appropriate organic compounds. For purposes of this disclosure, the heteroatoms, such as nitrogen and oxygen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. Also, as used herein "substitution" or "substituted with" is meant to encompass configurations where one substituent is fused to another substituent. For example, an aryl group substituted with an aryl group (or vice versa) can mean that one aryl group is bonded to the second aryl group via a single sigma bond and also that the two aryl groups are fused, e.g., two carbons of one alkyl group are shared with two carbons of the other aryl group.

The term "alkyl" as used herein is a branched or unbranched saturated hydrocarbon group of 1 to 20 carbon atoms ($C_{1-20}$), such as methyl ($C_1$), ethyl ($C_2$), n-propyl ($C_3$), isopropyl ($C_3$), n-butyl ($C_4$), isobutyl ($C_5$), t-butyl ($C_5$), pentyl ($C_5$), hexyl ($C_6$), heptyl ($C_7$), octyl ($C_8$), nonyl ($C_9$), decyl ($C_{10}$), dodecyl ($C_{12}$), tetradecyl ($C_{14}$), hexadecyl ($C_{16}$), octadecyl ($C_{18}$), eicosyl ($C_{20}$), and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, azide, nitro, nitrile, or thiol, as described below. A "lower alkyl" is a branched or unbranched alkyl group with up to six carbon atoms ($C_{1-6}$), e.g., methyl, ethyl, propyl, isopropyl, butyl, isobutyl, t-butyl, pentyl, and hexyl. The term "$C_{1-10}$ alkyl" as used herein refers to a branched or unbranched alkyl with up to 10 carbon atoms, such as methyl, ethyl, n-propyl, isopropyl, n-butyl, isobutyl, 1-butyl, and the like or branched or unbranched hydrocarbon groups of carbon atoms that either contain double or triple carbon bonds. Other terms for a group of alkyl substituents, such as $C_{1-4}$ alkyl and $C_{1-8}$ alkyl, which are branched or unbranched hydrocarbon groups with 4 or 8 carbon atoms, respectively, are also used herein.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "alkyl halide" specifically refers to an alkyl group that is substituted with one or more halides, e.g., fluorine, chlorine, bromine, or iodine. Similarly, the term "aralkyl" refers to an alkyl group substituted with an aryl group. When "alkyl" is used in one sentence and a specific term such as "alkyl halide" or "aralkyl" is used in another, it is not meant to imply that the term "alkyl" does not also refer to specific terms such as "alkyl halide" or "aralkyl" and the like.

This practice is also used for other groups described herein. That is, while a term such as "heteroaryl" refers to both unsubstituted and substituted heteroaryl moieties, the substituted moieties can, in addition, be specifically identified herein; for example, a particular substituted heteroaryl can be referred to as, e.g., an "alkyl heteroaryl." Similarly, a substituted alkenyl can be, e.g., an "alkenyl halide," and the like. Again, the practice of using a general term, such as "heteroaryl," and a specific term, such as "alkyl heteroaryl," is not meant to imply that the general term does not also include the specific term.

The term "alkoxy" as used herein is an alkyl or cycloalkyl group bonded through an ether linkage; that is, an "alkoxy" group can be defined as —OR where R is alkyl or cycloalkyl as defined herein. A "lower alkoxy" is a $C_{1-6}$ alkoxy group with up to six carbon atoms, e.g., methoxy, ethoxy, propoxy, butoxy, pentoxy, and hexoxy. The term "$C_{1-10}$ alkoxy," as used herein, refers to a $C_{1-10}$ alkyl group as defined herein attached to the parent molecular group through an oxygen atom. The term $C_{1-4}$ alkoxy refers to $C_{1-4}$ alkyl groups as defined herein attached to the parent molecular group through an oxygen atom, and so forth.

The term "alkenyl" as used herein is a hydrocarbon group of from 2 to 20 carbon atoms with a structural formula containing at least one carbon-carbon double bond. Asymmetric structures such as $(R^1R^2)C=C(R^3R^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, azide, nitro, nitrile, or thiol. As with alkyl, the terms "lower alkenyl," "$C_{1-10}$ alkenyl," "$C_{1-4}$ alkenyl," and the like are similarly defined.

The term "alkynyl" as used herein is a hydrocarbon group of 2 to 20 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, azide, nitro, nitrile, or thiol. As with alkyl, the terms "lower alkynyl," "$C_{1-10}$ alkynyl," "$C_{1-4}$ alkynyl," and the like are similarly defined.

The term "aliphatic" as used herein refers to a non-aromatic hydrocarbon group and includes branched and unbranched alkyl, alkenyl, or alkynyl groups.

The term "aryl" as used herein is a group that contains any carbon-based aromatic group including, but not limited to, benzene, benzyl, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, sulfo-oxo, sulfonylamino, azide, nitro, nitrile, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, cyclooctyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, azide, nitrile, silyl, or thiol. The term "$C_{3-15}$ cycloalkyl" as applied herein is meant to include cyclic hydrocarbon chains. Examples of these cyclic hydrocarbon chains include cyclopropane, cyclobutane, cyclopentane, cyclohexane, cycloheptane, cyclooctane, cyclononane, cyclodecane, cycloundecane, etc.

The term "cycloalkenyl" as used herein is a non-aromatic carbon-based ring composed of at least three carbon atoms and contains at least one double bound, e.g., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, azide, nitrile, or thiol.

The term "cyclic group" is used herein to refer to either aryl groups (e.g., heteraryl, biaryl), non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The terms "amine" or "amino," as used herein, refers to —NH$_2$ or derivatives thereof formed by independent replacement of one or both hydrogen atoms thereon with a substituent or substituents independently selected from alkyl, alkanoyl, aryl, arylalkyl, cycloalkyl, cycloalkylalkyl, heteroaryl, heteroarylalkyl, and an amino protecting group. The term "$C_{1-10}$ alkylamino," as used herein, refers to a $C_{1-10}$ alkyl group, as defined herein, to which is attached at least one amino substituent. The term "$C_{2-12}$ dialkylamino," as used herein, refers to two $C_{1-10}$ alkyl groups, as defined herein, that are attached to an amino substituent.

The term "$C_{1-10}$ fluoroalkyl," as used herein, refers to a $C_{1-10}$ alkyl group, as defined herein, to which is attached at least one fluorine substituent.

The term "$C_{1-10}$ perfluoroalkyl," as used herein, refers to a $C_{1-10}$ alkyl group in which all of the hydrogen atoms have been replaced with fluorine atoms.

The term "carboxylic acid" as used herein is represented by the formula —C(O)OH. The term "carboxylate" is a carboxylic acid that has been deprotonated, i.e., —C(O)O—. Protonation and deprotonation can be achieved by changes in pH. The terms "carboxylic acid" and "carboxylate" are understood to be interchangeable. Also, throughout the specification the abbreviation C(O) is understood to represent a carbonyl group C=O.

The term "ester" as used herein is represented by the formula —OC(O)R or —C(O)OR, where R can be a substituted or unsubstituted alkyl, cycloalkyl, alkenyl, cycloalkenyl, alkynyl, cycloalkynyl, aryl, or heteroaryl group as described herein.

The term "ether" as used herein is represented by the formula ROR, where each R can be, independently of the other, a substituted or unsubstituted alkyl, cycloalkyl, alkenyl, cycloalkenyl, alkynyl, cycloalkynyl, aryl, or heteroaryl group described herein.

The term "halide" as used herein refers to the halogens fluorine, chlorine, bromine, and iodine.

The term "hydroxyl" as used herein is represented by the formula —OH.

The term "ketone" as used herein is represented by the formula RC(O)R, where each R can be, independently of the other, a substituted or unsubstituted alkyl, cycloalkyl, alkenyl, cycloalkenyl, alkynyl, cycloalkynyl, aryl, or heteroaryl group as described herein.

The term "nitro" as used herein is represented by the formula —$NO_2$.

The term "nitrile" as used herein is represented by the formula —CN.

The term "thiol" as used herein is represented by the formula —SH.

The term "isocyanate" as used herein is represented by the formula —NCO.

The term "sulfo-oxo" as used herein is represented by the formulas —S(O)R, —S(O)$_2$R, —OS(O)$_2$R, or —OS(O)$_2$OR, where R can be hydrogen or a substituted or unsubstituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$R, where R can be hydrogen or a substituted or unsubstituted alkyl, cycloalkyl, alkenyl, cycloalkenyl, alkynyl, cycloalkynyl, aryl, or heteroaryl group as described herein. The term "sulfone" as used herein is represented by the formula RS(O)$_2$R, where each R can be, independently, a substituted or unsubstituted alkyl, cycloalkyl, alkenyl, cycloalkenyl, alkynyl, cycloalkynyl, aryl, or heteroaryl group as described herein. The term "sulfoxide" as used herein is represented by the formula RS(O)R, where each R can be, independently, a substituted or unsubstituted alkyl, cycloalkyl, alkenyl, cycloalkenyl, alkynyl, cycloalkynyl, aryl, or heteroaryl group as described herein.

The abbreviation Mu refers to morpholinocarbonyl, O(CH$_2$CH$_2$)$_2$N—CO—. The abbreviation PhPr refers to phenylpropanoyl, and Hph to homophenylalanine. The abbreviation Pip-CO— refers to an N-piperidylcarbonyl group.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixtures.

Reference will now be made in detail to specific aspects of the disclosed materials, compounds, compositions, components, devices, articles, and methods, examples of which are illustrated in the following description and examples, and in the figures and their previous and following description.

Materials and Compositions

Disclosed herein are compositions that comprise a class of peptidyl α-ketoamides that can be used for selectively inhibiting cysteine proteases such as calpain and generally inhibiting all cysteine proteases. Cysteine proteases are involved in numerous disease states and inhibitors for these enzymes can be used therapeutically for the treatment of diseases involving cysteine proteases. It has been discovered and is disclosed herein that peptidyl α-ketoamides can be constructed to inhibit selectively cysteine proteases or groups of cysteine proteases. Ketoamides with aromatic amino acid residues in the P1 site would be good inhibitors for cysteine proteases such as papain, cathepsin B, and calpain I and II. Thus, they would have utility as anticancer agents. Ketoamides with either aromatic amino acid residues or small hydrophobic alkyl amino acid residues at P1 are good inhibitors of calpain I and II. Ketoamides with small alkyl amino acid residues such as Leu or Val at P2 are also good inhibitors of the calpains. Ketoamides which contain a heterocyclic base or choline-like moieties also are not only potent inhibitors for calpain, but have the ability to be transported into cells particularly in the nervous system. The ketoamides which are calpain inhibitors would be useful as neuroprotectants and can be used as therapeutics for the treatment of neurodegeneration, stroke, restenosis, ALS, muscular dystrophy, and related diseases.

In discussing the interactions of peptides with cysteine proteases, the nomenclature of Schechter and Berger (*Biochem. Biophys. Res. Commun.* 27:157-62, 1967) is utilized throughout this specification. The individual amino acid residues of a substrate or an inhibitor are designated P1, P2, etc. and the corresponding subsites of the enzyme are designated S1, S2, etc. The scissile bond of the substrate is S1-S1'. The primary substrate recognition site of serine proteases is S1. The most important recognition subsites of cysteine proteases such as calpain are S1 and S2. With cysteine proteases, there are additional recognition sites at the prime subsites such as S1' and S2'.

Amino acid residues and blocking groups are designated using standard abbreviations (see *J. Biol. Chem.* 260:14-42, 1985, for nomenclature rules, which is incorporated by reference herein). An amino acid residue (AA) in a peptide or inhibitor structure refers to the part structure —NH—CHR$^1$—CO—, where R$^1$ is the side chain of the amino acid residue AA. An amino acid α-ketoester residue would be designated -AA-CO—OR, which represents the part structure —NH—CHR$^1$—CO—CO—OR. Thus, the ethyl ketoester derived from benzoyl alanine would be designated Bz-Ala-CO—OEt which represents C$_6$H$_5$CO—NH—CHMe-CO—CO—OEt. Likewise, peptide ketoamide residues would be designated -AA-CO—NH—R respectively. Thus, the ethylketo amide derived from Z-Leu-Phe-OH would be designated Z-Leu-Phe-CO—NH-Et which represents C$_6$H$_5$CH$_2$OCO—NH—CH(CH$_2$CHMe$_2$)—CO—NH—CH(CH$_2$Ph)-CO—CO—NH-Et.

The peptide alpha-ketoamides of this composition are abbreviated as M-AA$^2$-AA$^1$-CO—NH—(CH$_2$)$_n$—R$^3$. The ketoamide portion of the molecule, -AA$^1$-CO—NH—(CH$_2$)$_n$—R$^3$, is equivalent to —NHCHR$^1$CO—CO—

NH—(CH$_2$)$_6$—R$^3$ where the R$^1$ is the side chain of AA$^1$. Thus the peptide alpha-ketoamide AK295 is abbreviated as Z-Leu-Abu-CONH—(CH$_2$)$_3$-4-morpholinyl (AK295). The Z is a benzyloxycarbonyl group, Leu is a leucine residue, Abu is an alpha-aminobutanoic acid residue, the ketone carbonyl group is part of the Abu residue, CONH is the amide of the α-ketoamide, and the 4-morpholinyl group is a morpholine bound to the methylene chair through the nitrogen atom of the morpholine ring. The structure of the peptide α-ketoamide AK295, abbreviated as Z-Leu-Abu-CONH—(CH$_2$)$_3$-4-morpholinyl is shown below.

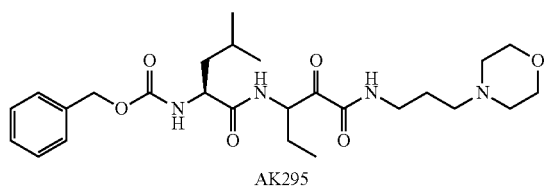 [SMILES: CCC(NC(=O)[C@H](CC(C)C)NC(=O)OCc1ccccc1)C(=O)C(=O)NCCCN1CCOCC1 ; "AK295"]

AK295

Specific Compositions

Disclosed herein is a class of dipeptide α-ketoamides that has the formula M-AA$^2$-AA$^1$-CO—NH—(CH$_2$)$_n$—R$^3$ (referred to herein as "Formula I"). This formula is based on the nomenclature of Schechter and Berger discussed above. Formula I can also be represented by the following structural formula, where R$^2$ and R$^1$ represent the side chains of amino acid residues AA$^2$ and AA$^1$ respectively.

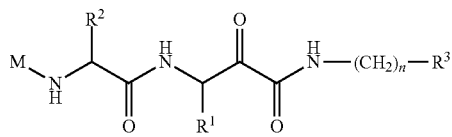

Disclosed herein are compositions of Formula I, M-AA$^2$-AA$^1$-CO—NH—(CH$_2$)$_n$—R$^3$, or a pharmaceutically acceptable salt, wherein M is selected from the group consisting of Y—FG,

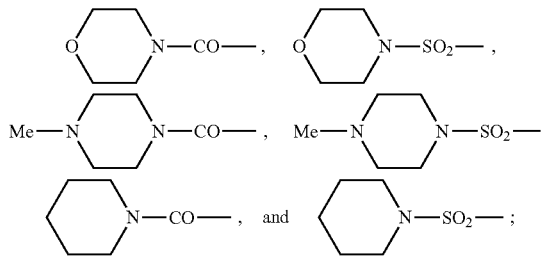

FG is selected from the group consisting of —CO—, —O—CO—, —NH—CO—, —SO$_2$—, —NH—SO$_2$—, —NH—CS—, H—CO—, NH$_2$—CO—NH$_2$—SO$_2$—, and NH$_2$—CS;

Y is selected from the group consisting of C$_{1-8}$ alkyl, C$_{3-15}$ cycloalkyl, C$_{1-4}$ alkyl monosubstituted with phenyl, C$_{1-4}$ alkyl disubstituted with phenyl, C$_{1-4}$ alkyl monosubstituted with Ar, C$_{1-4}$ alkyl monosubstituted with 1-naphthyl, C$_{1-4}$ alkyl monosubstituted with 2-naphthyl, and Ar;

Ar is selected from the group consisting of phenyl, phenyl monosubstituted with J, phenyl disubstituted with J, 1-naphthyl, 1-naphthyl monosubstituted with J, 2-naphthyl, 2-naphthyl monosubstituted with J, 2-pyridyl, 3-pyridyl, and 4-pyridyl;

J is selected from the group consisting of halogen, OH, CN, NO$_2$, NH$_2$, COOH, CO$_2$Me, CO$_2$Et, CF$_3$, C$_{1-6}$ alkyl, C$_{1-4}$ alkoxy, and, C$_{1-4}$ perfluoroalkyl;

AA$^2$ is an amino acid with the L configuration, D configuration, or DL configuration at the α-carbon and is selected from the group consisting of alanine, valine, leucine, isoleucine, proline, histidine, methionine, methionine sulfoxide, phenylalanine, serine, threonine, phenylglycine, norleucine, norvaline, alpha-aminobutyric acid, O-methylserine, O-ethylserine, S-methylcysteine, S-ethylcysteine, S-benzylcysteine, NH$_2$—CH(CH$_2$CHEt$_2$)—COOH, alpha-aminoheptanoic acid, NH$_2$—CH(CH$_2$-cyclohexyl)-COOH, NH$_2$—CH(CH$_2$-cyclopentyl)-COOH, NH$_2$—CH(CH$_2$-cyclobutyl)-COOH, NH$_2$—CH(CH$_2$-cyclopropyl)-COOH, 5,5,5-trifluoroleucine, α-aminohexanoic acid, thiaproline, and hexafluoroleucine;

AA$^1$ is an amino acid with the L configuration, D configuration, or DL configuration at the α-carbon and is selected from the group consisting of alanine, valine, leucine, isoleucine, proline, histidine, methionine, methionine sulfoxide, phenylalanine, arginine, lysine, tryptophan, glycine, serine, threonine, cysteine, tyrosine, asparagine, glutamine, aspartic acid, glutamic acid, phenylglycine, norleucine, norvaline, alpha-aminobutyric acid, O-methylserine, O-ethylserine, S-methylcysteine, S-ethylcysteine, S-benzylcysteine, NH$_2$—CH(CH$_2$CHEt$_2$)—COOH, alpha-aminoheptanoic acid, NH$_2$—CH(CH$_2$-1-naphthyl)-COOH, NH$_2$—CH(CH$_2$-2-naphthyl)-COOH, NH$_2$—CH(CH$_2$-cyclohexyl)-COOH, NH$_2$—CH(CH$_2$-cyclopentyl)-COOH, NH$_2$—CH(CH$_2$-cyclobutyl)-COOH, NH$_2$—CH(CH$_2$-cyclopropyl)-COOH, 5,5,5-trifluoroleucine, homophenylalanine, hexafluoroleucine, α-aminohexanoic acid, phenylalanine monosubstituted on the phenyl group with K, and homophenylalanine monosubstituted on the phenyl group with K;

K is selected from the group consisting of halogen, C$_{1-6}$ alkyl, and C$_{1-4}$ alkoxy;

n is an integer from 1 to 5;

R$^3$ is selected from the group consisting of

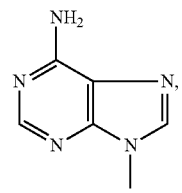 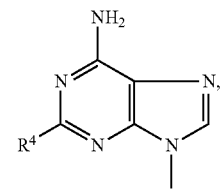

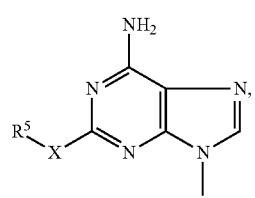 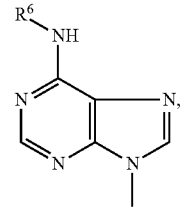

-continued

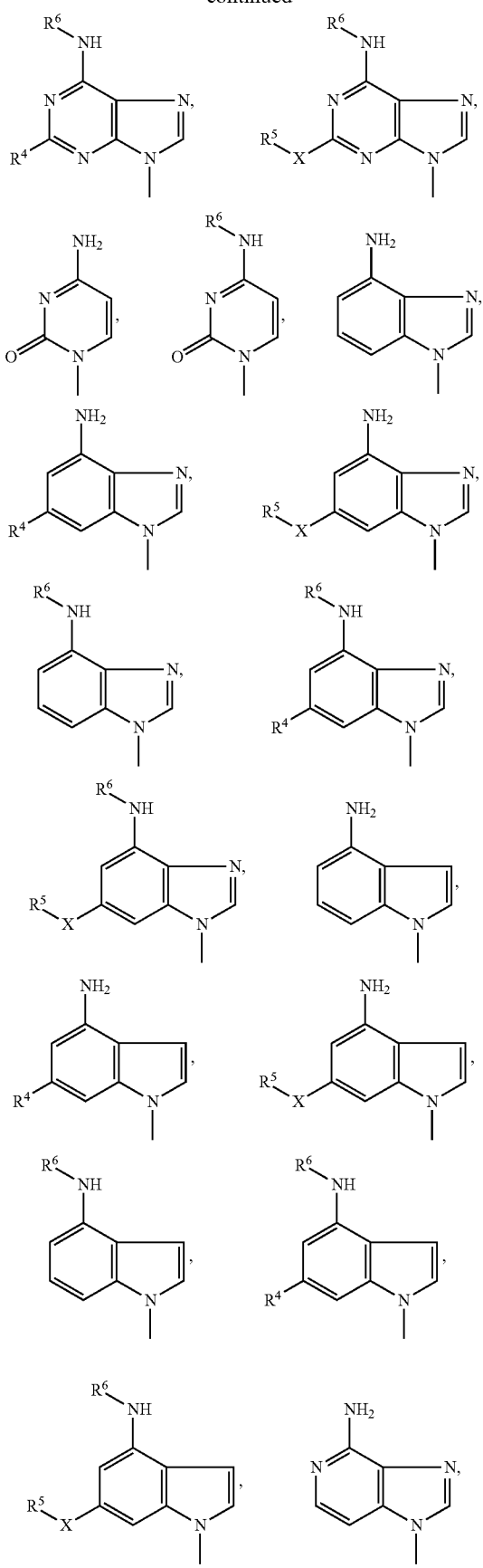
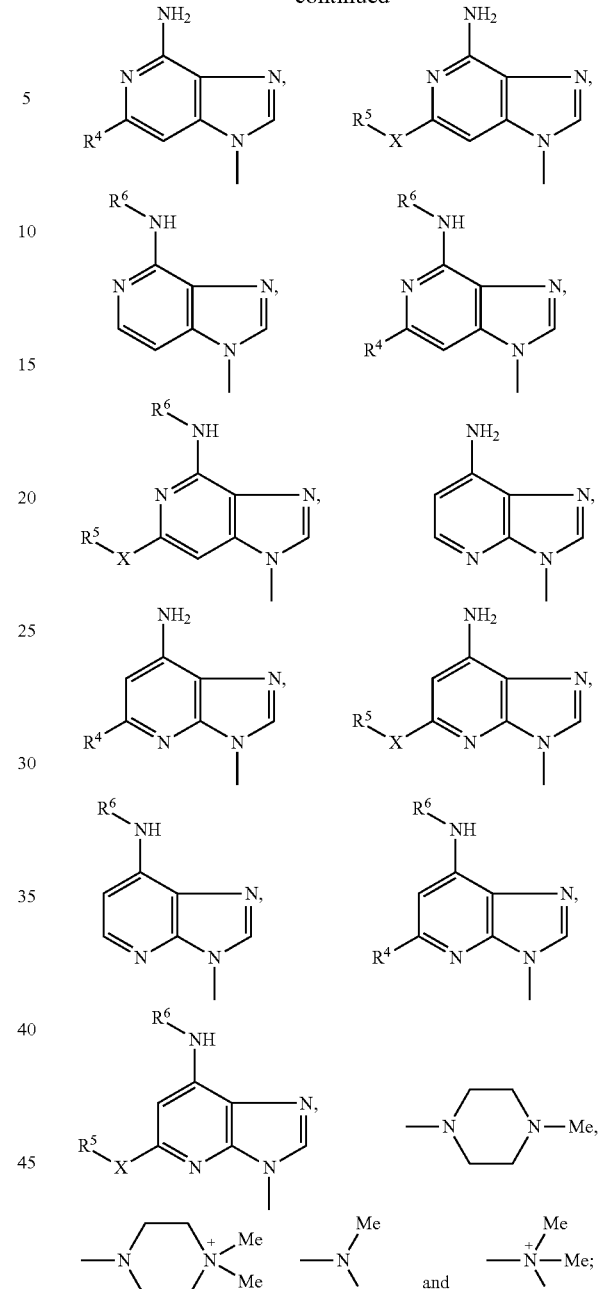

X is selected from O, NH, and S;

$R^4$ is selected from the group consisting of $C_{1-6}$ alkyl, phenyl, and benzyl;

$R^5$ is selected from the group consisting of $C_{1-6}$ alkyl, phenyl, and benzyl; and $R^6$ is selected from the group consisting of $C_{1-6}$ alkyl, phenyl, and benzyl.

Exemplary Structures

In one example of the disclosed dipeptide α-ketoamides, the compound is benzyl (2S)-1-(1-(3-(6-amino-9H-purin-9-yl)propylamino)-1,2-dioxopentan-3-ylamino)-4-methyl-1-oxopentan-2-ylcarbamate. This compound is shown in Structure A.

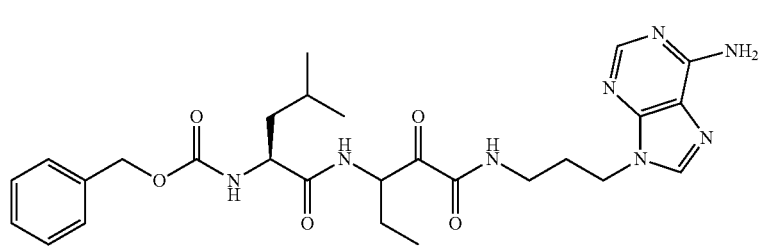

This structure corresponds to Formula I when M is Y—FG, FG is O—CO—, Y is benzyl, AA² is leucine, AA¹ is α-aminobutanoic acid (Abu), n is 3, and R³ is:

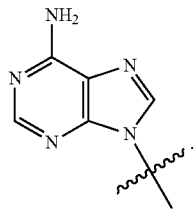

Further examples of peptide α-ketoamides disclosed herein include, but are not limited to, the compounds in Table 1.

TABLE 1

Z-Leu-Abu-CONH—(CH₂)₃-adenin-9-yl,
Z-Leu-Phe-CONH—(CH₂)₃-adenin-9-yl,
Z-Leu-Hph-CONH—(CH₂)₃-adenin-9-yl,
Z-Val-Abu-CONH—(CH₂)₃-adenin-9-yl,
Z-Val-Phe-CONH—(CH₂)₃-adenin-9-yl,
Z-Val-Hph-CONH—(CH₂)₃-adenin-9-yl,
Z-Leu-Abu-CONH—(CH₂)₃-2-methyladenin-9-yl,
Z-Leu-Phe-CONH—(CH₂)₃-2-methyladenin-9-yl,
Z-Leu-Hph-CONH—(CH₂)₃-2-methyladenin-9-yl,
Z-Val-Abu-CONH—(CH₂)₃-2-methyladenin-9-yl,
Z-Val-Phe-CONH—(CH₂)₃-2-methyladenin-9-yl,
Z-Val-Hph-CONH—(CH₂)₃-2-methyladenin-9-yl,
Z-Leu-Abu-CONH—(CH₂)₃-2-methoxyadenin-9-yl,
Z-Leu-Phe-CONH—(CH₂)₃-2-methoxyadenin-9-yl,
Z-Leu-Hph-CONH—(CH₂)₃-2-methoxyadenin-9-yl,
Z-Val-Abu-CONH—(CH₂)₃-2-methoxyadenin-9-yl,
Z-Val-Phe-CONH—(CH₂)₃-2-methoxyadenin-9-yl,
Z-Val-Hph-CONH—(CH₂)₃-2-methoxyadenin-9-yl,
Z-Leu-Abu-CONH—(CH₂)₃-cytosin-3-yl,
Z-Leu-Phe-CONH—(CH₂)₃-cytosin-3-yl,
Z-Leu-Hph-CONH—(CH₂)₃-cytosin-3-yl,
Z-Val-Abu-CONH—(CH₂)₃-cytosin-3-yl,
Z-Val-Phe-CONH—(CH₂)₃-cytosin-3-yl,
Z-Val-Hph-CONH—(CH₂)₃-cytosin-3-yl,
Z-Leu-Abu-CONH—(CH₂)₃-(4-methylpiperazin-1-yl),
Z-Leu-Phe-CONH—(CH₂)₃-(4-methylpiperazin-1-yl),
Z-Leu-Hph-CONH—(CH₂)₃-(4-methylpiperazin-1-yl),
Z-Val-Abu-CONH—(CH₂)₃-(4-methylpiperazin-1-yl),
Z-Val-Phe-CONH—(CH₂)₃-(4-methylpiperazin-1-yl),
Z-Val-Hph-CONH—(CH₂)₃-(4-methylpiperazin-1-yl),
Z-Leu-Abu-CONH—(CH₂)₃—N(CH₃)₂,
Z-Leu-Phe-CONH—(CH₂)₃—N(CH₃)₂,
Z-Leu-Hph-CONH—(CH₂)₃—N(CH₃)₂,
Z-Val-Abu-CONH—(CH₂)₃—N(CH₃)₂,
Z-Val-Phe-CONH—(CH₂)₃—N(CH₃)₂,
Z-Val-Hph-CONH—(CH₂)₃—N(CH₃)₂,
Z-Leu-Abu-CONH—(CH₂)₂—N(CH₃)₂,
Z-Leu-Phe-CONH—(CH₂)₂—N(CH₃)₂,
Z-Leu-Hph-CONH—(CH₂)₂—N(CH₃)₂,
Z-Val-Abu-CONH—(CH₂)₂—N(CH₃)₂,
Z-Val-Phe-CONH—(CH₂)₂—N(CH₃)₂, TABLE 1-continued Z-Val-Hph-CONH—(CH₂)₂—N(CH₃)₂,
Mu-Leu-Abu-CONH—(CH₂)₃-adenin-9-yl,
Mu-Leu-Phe-CONH—(CH₂)₃-adenin-9-yl,
Mu-Leu-Hph-CONH—(CH₂)₃-adenin-9-yl,
Mu-Val-Abu-CONH—(CH₂)₃-adenin-9-yl,
Mu-Val-Phe-CONH—(CH₂)₃-adenin-9-yl,
Mu-Val-Hph-CONH—(CH₂)₃-adenin-9-yl,
Mu-Leu-Abu-CONH—(CH₂)₃-2-methyladenin-9-yl,
Mu-Leu-Phe-CONH—(CH₂)₃-2-methyladenin-9-yl,
Mu-Leu-Hph-CONH—(CH₂)₃-2-methyladenin-9-yl,
Mu-Val-Abu-CONH—(CH₂)₃-2-methyladenin-9-yl,
Mu-Val-Phe-CONH—(CH₂)₃-2-methyladenin-9-yl,
Mu-Val-Hph-CONH—(CH₂)₃-2-methyladenin-9-yl,
Mu-Leu-Abu-CONH—(CH₂)₃-2-methoxyadenin-9-yl,
Mu-Leu-Phe-CONH—(CH₂)₃-2-methoxyadenin-9-yl,
Mu-Leu-Hph-CONH—(CH₂)₃-2-methoxyadenin-9-yl,
Mu-Val-Abu-CONH—(CH₂)₃-2-methoxyadenin-9-yl,
Mu-Val-Phe-CONH—(CH₂)₃-2-methoxyadenin-9-yl,
Mu-Val-Hph-CONH—(CH₂)₃-2-methoxyadenin-9-yl,
Mu-Leu-Abu-CONH—(CH₂)₃-cytosin-3-yl,
Mu-Leu-Phe-CONH—(CH₂)₃-cytosin-3-yl,
Mu-Leu-Hph-CONH—(CH₂)₃-cytosin-3-yl,
Mu-Val-Abu-CONH—(CH₂)₃-cytosin-3-yl,
Mu-Val-Phe-CONH—(CH₂)₃-cytosin-3-yl,
Mu-Val-Hph-CONH—(CH₂)₃-cytosin-3-yl,
Mu-Leu-Abu-CONH—(CH₂)₃-(4-methylpiperazin-1-yl),
Mu-Leu-Phe-CONH—(CH₂)₃-(4-methylpiperazin-1-yl),
Mu-Leu-Hph-CONH—(CH₂)₃-(4-methylpiperazin-1-yl),
Mu-Val-Abu-CONH—(CH₂)₃-(4-methylpiperazin-1-yl),
Mu-Val-Phe-CONH—(CH₂)₃-(4-methylpiperazin-1-yl),
Mu-Val-Hph-CONH—(CH₂)₃-(4-methylpiperazin-1-yl),
Mu-Leu-Abu-CONH—(CH₂)₃—N(CH₃)₂,
Mu-Leu-Phe-CONH—(CH₂)₃—N(CH₃)₂,
Mu-Leu-Hph-CONH—(CH₂)₃—N(CH₃)₂,
Mu-Val-Abu-CONH—(CH₂)₃—N(CH₃)₂,
Mu-Val-Phe-CONH—(CH₂)₃—N(CH₃)₂,
Mu-Val-Hph-CONH—(CH₂)₃—N(CH₃)₂,
Mu-Leu-Abu-CONH—(CH₂)₂—N(CH₃)₂,
Mu-Leu-Phe-CONH—(CH₂)₂—N(CH₃)₂,
Mu-Leu-Hph-CONH—(CH₂)₂—N(CH₃)₂,
Mu-Val-Abu-CONH—(CH₂)₂—N(CH₃)₂,
Mu-Val-Phe-CONH—(CH₂)₂—N(CH₃)₂,
Mu-Val-Hph-CONH—(CH₂)₂—N(CH₃)₂,
Pip-CO-Leu-Abu-CONH—(CH₂)₃-adenin-9-yl,
Pip-CO-Leu-Phe-CONH—(CH₂)₃-adenin-9-yl,
Pip-CO-Leu-Hph-CONH—(CH₂)₃-adenin-9-yl,
Pip-CO-Val-Abu-CONH—(CH₂)₃-adenin-9-yl,
Pip-CO-Val-Phe-CONH—(CH₂)₃-adenin-9-yl,
Pip-CO-Val-Hph-CONH—(CH₂)₃-adenin-9-yl,
Pip-CO-Leu-Abu-CONH—(CH₂)₃-2-methyladenin-9-yl,
Pip-CO-Leu-Phe-CONH—(CH₂)₃-2-methyladenin-9-yl,
Pip-CO-Leu-Hph-CONH—(CH₂)₃-2-methyladenin-9-yl,
Pip-CO-Val-Abu-CONH—(CH₂)₃-2-methyladenin-9-yl,
Pip-CO-Val-Phe-CONH—(CH₂)₃-2-methyladenin-9-yl,
Pip-CO-Val-Hph-CONH—(CH₂)₃-2-methyladenin-9-yl,
Pip-CO-Leu-Abu-CONH—(CH₂)₃-2-methoxyadenin-9-yl,
Pip-CO-Leu-Phe-CONH—(CH₂)₃-2-methoxyadenin-9-yl,
Pip-CO-Leu-Hph-CONH—(CH₂)₃-2-methoxyadenin-9-yl,
Pip-CO-Val-Abu-CONH—(CH₂)₃-2-methoxyadenin-9-yl,
Pip-CO-Val-Phe-CONH—(CH₂)₃-2-methoxyadenin-9-yl,
Pip-CO-Val-Hph-CONH—(CH₂)₃-2-methoxyadenin-9-yl,
Pip-CO-Leu-Abu-CONH—(CH₂)₃-cytosin-3-yl,
Pip-CO-Leu-Phe-CONH—(CH₂)₃-cytosin-3-yl,
Pip-CO-Leu-Hph-CONH—(CH₂)₃-cytosin-3-yl, TABLE 1-continued Pip-CO-Val-Abu-CONH—(CH$_2$)$_3$-cytosin-3-yl,
Pip-CO-Val-Phe-CONH—(CH$_2$)$_3$-cytosin-3-yl,
Pip-CO-Val-Hph-CONH—(CH$_2$)$_3$-cytosin-3-yl,
Pip-CO-Leu-Abu-CONH—(CH$_2$)$_3$-(4-methylpiperazin-1-yl),
Pip-CO-Leu-Phe-CONH—(CH$_2$)$_3$-(4-methylpiperazin-1-yl),
Pip-CO-Leu-Hph-CONH—(CH$_2$)$_3$-(4-methylpiperazin-1-yl),
Pip-CO-Val-Abu-CONH—(CH$_2$)$_3$-(4-methylpiperazin-1-yl),
Pip-CO-Val-Phe-CONH—(CH$_2$)$_3$-(4-methylpiperazin-1-yl),
Pip-CO-Val-Hph-CONH—(CH$_2$)$_3$-(4-methylpiperazin-1-yl),
Pip-CO-Leu-Abu-CONH—(CH$_2$)$_3$—N(CH$_3$)$_2$,
Pip-CO-Leu-Phe-CONH—(CH$_2$)$_3$—N(CH$_3$)$_2$,
Pip-CO-Leu-Hph-CONH—(CH$_2$)$_3$—N(CH$_3$)$_2$,
Pip-CO-Val-Abu-CONH—(CH$_2$)$_3$—N(CH$_3$)$_2$,
Pip-CO-Val-Phe-CONH—(CH$_2$)$_3$—N(CH$_3$)$_2$,
Pip-CO-Val-Hph-CONH—(CH$_2$)$_3$—N(CH$_3$)$_2$,
Pip-CO-Leu-Abu-CONH—(CH$_2$)$_2$—N(CH$_3$)$_2$,
Pip-CO-Leu-Phe-CONH—(CH$_2$)$_2$—N(CH$_3$)$_2$,
Pip-CO-Leu-Hph-CONH—(CH$_2$)$_2$—N(CH$_3$)$_2$,
Pip-CO-Val-Abu-CONH—(CH$_2$)$_2$—N(CH$_3$)$_2$,
Pip-CO-Val-Phe-CONH—(CH$_2$)$_2$—N(CH$_3$)$_2$,
Pip-CO-Val-Hph-CONH—(CH$_2$)$_2$—N(CH$_3$)$_2$,
PhPr-Leu-Abu-CONH—(CH$_2$)$_3$-adenin-9-yl,
PhPr-Leu-Phe-CONH—(CH$_2$)$_3$-adenin-9-yl,
PhPr-Leu-Hph-CONH—(CH$_2$)$_3$-adenin-9-yl,
PhPr-Val-Abu-CONH—(CH$_2$)$_3$-adenin-9-yl,
PhPr-Val-Phe-CONH—(CH$_2$)$_3$-adenin-9-yl,
PhPr-Val-Hph-CONH—(CH$_2$)$_3$-adenin-9-yl,
PhPr-Leu-Abu-CONH—(CH$_2$)$_3$-2-methyladenin-9-yl,
PhPr-Leu-Phe-CONH—(CH$_2$)$_3$-2-methyladenin-9-yl,
PhPr-Leu-Hph-CONH—(CH$_2$)$_3$-2-methyladenin-9-yl,
PhPr-Val-Abu-CONH—(CH$_2$)$_3$-2-methyladenin-9-yl,
PhPr-Val-Phe-CONH—(CH$_2$)$_3$-2-methyladenin-9-yl,
PhPr-Val-Hph-CONH—(CH$_2$)$_3$-2-methyladenin-9-yl,
PhPr-Leu-Abu-CONH—(CH$_2$)$_3$-2-methoxyadenin-9-yl,
PhPr-Leu-Phe-CONH—(CH$_2$)$_3$-2-methoxyadenin-9-yl,
PhPr-Leu-Hph-CONH—(CH$_2$)$_3$-2-methoxyadenin-9-yl,
PhPr-Val-Abu-CONH—(CH$_2$)$_3$-2-methoxyadenin-9-yl,
PhPr-Val-Phe-CONH—(CH$_2$)$_3$-2-methoxyadenin-9-yl,
PhPr-Val-Hph-CONH—(CH$_2$)$_3$-2-methoxyadenin-9-yl,
PhPr-Leu-Abu-CONH—(CH$_2$)$_3$-cytosin-3-yl,
PhPr-Leu-Phe-CONH—(CH$_2$)$_3$-cytosin-3-yl,
PhPr-Leu-Hph-CONH—(CH$_2$)$_3$-cytosin-3-yl,
PhPr-Val-Abu-CONH—(CH$_2$)$_3$-cytosin-3-yl,
PhPr-Val-Phe-CONH—(CH$_2$)$_3$-cytosin-3-yl,
PhPr-Val-Hph-CONH—(CH$_2$)$_3$-cytosin-3-yl,
PhPr-Leu-Abu-CONH—(CH$_2$)$_3$-(4-methylpiperazin-1-yl),
PhPr-Leu-Phe-CONH—(CH$_2$)$_3$-(4-methylpiperazin-1-yl),
PhPr-Leu-Hph-CONH—(CH$_2$)$_3$-(4-methylpiperazin-1-yl),
PhPr-Val-Abu-CONH—(CH$_2$)$_3$-(4-methylpiperazin-1-yl),
PhPr-Val-Phe-CONH—(CH$_2$)$_3$-(4-methylpiperazin-1-yl),
PhPr-Val-Hph-CONH—(CH$_2$)$_3$-(4-methylpiperazin-1-yl),
PhPr-Leu-Abu-CONH—(CH$_2$)$_3$—N(CH$_3$)$_2$,
PhPr-Leu-Phe-CONH—(CH$_2$)$_3$—N(CH$_3$)$_2$,
PhPr-Leu-Hph-CONH—(CH$_2$)$_3$—N(CH$_3$)$_2$,
PhPr-Val-Abu-CONH—(CH$_2$)$_3$—N(CH$_3$)$_2$,
PhPr-Val-Phe-CONH—(CH$_2$)$_3$—N(CH$_3$)$_2$,
PhPr-Val-Hph-CONH—(CH$_2$)$_3$—N(CH$_3$)$_2$,
PhPr-Leu-Abu-CONH—(CH$_2$)$_2$—N(CH$_3$)$_2$,
PhPr-Leu-Phe-CONH—(CH$_2$)$_2$—N(CH$_3$)$_2$,
PhPr-Leu-Hph-CONH—(CH$_2$)$_2$—N(CH$_3$)$_2$,
PhPr-Val-Abu-CONH—(CH$_2$)$_2$—N(CH$_3$)$_2$,
PhPr-Val-Phe-CONH—(CH$_2$)$_2$—N(CH$_3$)$_2$, and
PhPr-Val-Hph-CONH—(CH$_2$)$_2$—N(CH$_3$)$_2$.

The compounds disclosed here are unlike those of Donkor et al. ("Synthesis, calpain inhibitory activity, and cytotoxicity of P2-substituted proline and thiaproline peptidyl aldehydes and peptidyl alpha-ketoamides," *J. Med. Chem.* 49:5282-90, 2006), which discloses α-ketoamides with P2 proline and substituted proline residues. Donkor et al.'s ketoamides do not have a heterocyclic ring system or an amine or a quaternary amino R$^3$. They also have no nitrogens in the R$^3$ group.

Similarly, Lescop et al. ("Novel cell-penetrating alpha-keto-amide calpain inhibitors as potential treatment for muscular dystrophy," *Bioorg. Med. Chem. Lett.* 15:176-81, 2005) discloses α-ketoamides that possess a lipoyl moiety at the P3 position. These ketoamides do not have a heterocyclic ring system or an amine or a quaternary amino R$^3$. They also have no nitrogens in the R$^3$ group and disulfide linkage in M.

Donkor et al. ("Synthesis and calpain inhibitory activity of alpha-ketoamides with 2,3-methanoleucine stereoisomers at the P2 position," *Bioorg. Med. Chem. Lett.* 10:2497-500, 2000) discloses α-ketoamides with 2,3-methanoleucine stereoisomers at the P2 position. These ketoamides do not have a heterocyclic ring system or an amine or a quaternary amino R$^3$ group. These structures also have no nitrogens in the R$^3$ group. Further, Donkor et al.'s ketoamides have cyclopropane rings in AA$^2$.

Moreover, Weyermann et al. ("Synthesis and evaluation of calpain inhibitors carrying muscle cell targeting groups," *Lett. Drug Design & Discovery* 3:152-8, 2006) discloses α-ketoamides carrying different muscle cell targeting groups at the amino terminus. These ketoamides do not have a heterocyclic ring system or an amine or a quaternary amino R$^3$. These structures also have no nitrogens in the R$^3$ group. Weyermann et al.'s compounds also have amino acid residues at M.

Shirasaki et al. ("Exploration of orally available calpain inhibitors. Part 3: Dipeptidyl alpha-ketoamide derivatives containing pyridine moiety," *Bioorg. Med. Chem.* 14:5691-8, 2006) discloses α-ketoamides containing a pyridine moiety at P3. These ketoamides do not have a heterocyclic ring system or an amine or a quaternary amino R$^3$. These structures also have no nitrogens in the R$^3$ group. Shirasaki et al.'s compounds also have a cyclopropane ring and no spacer in place of —(CH$_2$)$_n$—R$^3$.

Shirasaki et al. ("Exploration of orally available calpain inhibitors: peptidyl alpha-ketoamides containing an amphiphile at P3 site," *Bioorg. Med. Chem.* 13:4473-84, 2005) discloses α-ketoamides with an amphiphile at the P3 position. These ketoamides do not have a heterocyclic ring system or an amine or a quaternary amino as R$^3$. These structures also have no nitrogens in the R$^3$ group.

Lee et al. ("Synthesis and biological evaluation of chromone carboxamides as calpain inhibitors," *Bioorg. Med. Chem. Lett.* 15:2857-60, 2005) discloses α-ketoamides containing chromone derivatives in the P2-P3 region. These ketoamides do not have a heterocyclic ring system or an amine or a quaternary amino R$^3$. Lee et al.'s structures also have no nitrogens in the R$^3$ group. These compounds are not dipeptides and do not have an AA$^2$ in their structures.

Bihovsky et al. ("1,2-Benzothiazine 1,1-dioxide alpha-ketoamide analogues as potent calpain I inhibitors" *Bioorg. Med. Chem. Lett.* 14:1035-8, 2004) discloses 1,2-benzothiazine 1,1-dioxide α-ketoamides as calpain I inhibitors. These ketoamides do not have a heterocyclic ring system or an amine or a quaternary amino R$^3$. These structures also have no nitrogens in the R$^3$ group. Bihovsky et al.'s compounds are not dipeptides and do not have AA$^2$ in their structures.

Donkor et al. (Design, synthesis, molecular modeling studies, and calpain inhibitory activity of novel alpha-ketoamides incorporating polar residues at the P1'-position," *J. Med. Chem.* 47:72-9, 2004) discloses α-ketoamides containing stereoisoremic residues with different electronic properties at the P1' position. These ketoamides do not have a heterocyclic ring system or an amine or a quaternary amino R$^3$. These structures also have no nitrogens in the R$^3$ group. Also, Donkor et al.'s compounds have functional groups or heteroatoms on —(CH$_2$)$_n$—R$^3$.

Lubisch et al. ("Benzoylalanine-derived ketoamides carrying vinylbenzyl amino residues: discovery of potent water-soluble calpain inhibitors with oral bioavailability," *J. Med. Chem.* 46:2404-12, 2003) discloses α-ketoamides containing vinylbenzyl amino residues in the P2-P3 position. These ketoamides do not have a heterocyclic ring system or an amine or a quaternary amino $R^3$. These structures also have no nitrogens in the $R^3$ group. Lubisch et al.'s compounds are not dipeptides and do not have $AA^2$ in their structures.

Lubisch et al. ("Discovery of phenyl alanine derived ketoamides carrying benzoyl residues as novel calpain inhibitors," *Bioorg. Med. Chem. Lett.* 12:1335-8, 2002) discloses α-ketoamides carrying a benzoyl residue. These ketoamides do not have a heterocyclic ring system or an amine or a quaternary amino $R^3$. These structures also have no nitrogens in the $R^3$ group. Lubisch et al.'s compounds are not dipeptides and do not have $AA^2$ in their structures.

Chatterjee et al. (P2-achiral, P'-extended alpha-ketoamide inhibitors of calpain I," *Bioorg. Med. Chem. Lett.* 9:2371-4, 1999) discloses $P_2$-achiral, P'-spanning α-ketoamide inhibitors. These ketoamides do not have a heterocyclic ring system or a amine or a quaternary amino $R^3$. These structures also have no nitrogens in the $R^3$ group. Chatterjee et al.'s compounds are not dipeptides and do not have $AA^2$ in their structures.

Donkor ("A survey of calpain inhibitors," *Curr. Med. Chem.* 7:1171-88, 2000) reviews calpain inhibitors including ketoamides. The ketoamides disclosed in the review do not have a heterocyclic ring system or an amine or a quaternary amino $R^3$. The structures also have no nitrogens in the $R^3$ group.

Further, a series of ketoamides have been synthesized as inhibitors for cathepsin K. However, these ketoamides do not have a heterocyclic ring system or an amine or a quaternary amino $R^3$. Their structures also have no nitrogens in the $R^3$ group. These compounds are not dipeptides and they do not have $AA^2$ in their structures. References are Catalano et al., "Design of small molecule ketoamide-based inhibitors of cathepsin K," *Bioorg. Med. Chem. Lett.* 14:719-22, 2004; Tavares et al., "Ketoamide-based inhibitors of cysteine protease, cathepsin K: P3 modifications," *J. Med. Chem.* 47:5057-68, 2004; Tavares et al., "Potent and selective ketoamide-based inhibitors of cysteine protease, cathepsin K," *J. Med. Chem.* 47:5049-56, 2004; Barrett et al., "Novel, potent P2-P3 pyrrolidine derivatives of ketoamide-based cathepsin K inhibitors," *Bioorg. Med. Chem. Lett.* 16:1735-9, 2006; Barrett et al., "P2-P3 conformationally constrained ketoamide-based inhibitors of cathepsin K," *Bioorg. Med. Chem. Lett.* 15:3540-6, 2005; Barrett et al., "A structural screening approach to ketoamide-based inhibitors of cathepsin K," *Bioorg. Med. Chem. Lett.* 15:2209-13, 2005; Barrett et al., "Potent and selective P2-P3 ketoamide inhibitors of cathepsin K with good pharmacokinetic properties via favorable P1', P1, and/or P3 substitutions," *Bioorg. Med. Chem. Lett.* 14:4897-902, 2004; and Barrett et al., "Orally bioavailable small molecule ketoamide-based inhibitors of cathepsin K," *Bioorg. Med. Chem. Lett.* 14:2543-6, 2004, which are each incorporated by reference herein in their entireties.

Synthetic Methods

The synthesis of the compositions disclosed herein comprises several steps: 1) synthesis of dipeptide precursors, 2) synthesis of dipeptide esters and acids, 3) synthesis of precursor amines, and 4) synthesis of the new peptide ketoamides. Each of these steps is discussed below.

1. Synthesis of Peptide Precursors

The precursor peptide can be prepared using standard peptide chemistry which is well described in publications such as *The Peptides, Analysis, Synthesis, Biology*, Vol. 1-9, published in 1979-1987 by Academic Press and Houben-Weyl Methoden der Organischen Chemie, Vol. 15, Parts 1 and 2, *Synthese von Peptiden*, published by Georg Thieme Verlag, Stuttgart in 1974 (both references are incorporated by reference herein in their entireties for their teachings of peptide syntheses).

The M-group of Formula I can be introduced using a number of different reaction schemes. For example it can be introduced directly on an amino acid as shown in Scheme 1 (top), or the M-group can be introduced by reaction with an amino acid ester, followed by removal of the ester group by hydrolysis to give the same product (Scheme 1, bottom).

Scheme 1. Synthesis of M-substituted amino acid precursors,
$M-AA^2-OH$ or $M-AA^2-OR'$.

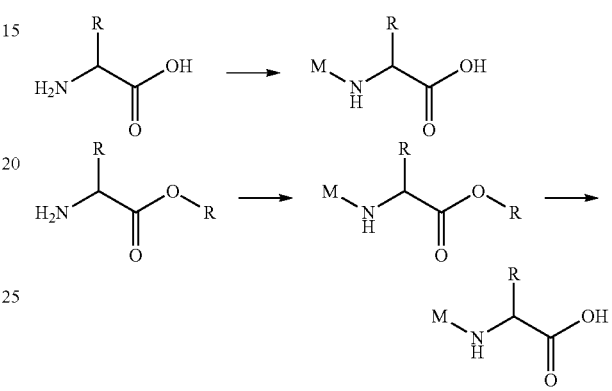

The techniques for introduction of the M-group are well documented in The Peptides, Houben-Weyl, and many other textbooks on organic synthesis. For example reaction with cyanate or p-nitrophenyl cyanate introduces a carbamyl group ($M=NH_2CO$—). Reaction with MeNHCOCl introduces the MeNHCO— group. Reaction with p-nitrophenyl thiocarbamate introduces a thio carbamyl group ($M=NH_2CS$—). Reaction with $NH_2SO_2Cl$ introduces the $NH_2SO_2$— group. Reaction with $MeNHSO_2Cl$ introduces the $MeNHSO_2$-group. Reaction with a substituted alkyl or aryl isocyanate introduces the Y—NH—CO— group where Y is a substituted alkyl or aryl group. Reaction with a substituted alkyl or aryl isothiocyanate introduces the Y—NH—CS— group where Y is a substituted alkyl or aryl group. Reaction with Y—$SO_2$—Cl introduces the Y—$SO_2$— group. Reaction with a substituted alkyl or aryl acid chloride introduces an acyl group ($M=Y$—CO—). For example, reaction with Ph-$CH_2CH_2$—CO—Cl gives the Y—CO— group where Y is a $C_3$ alkyl substituted with a phenyl group. Reaction with a substituted alkyl or aryl thioacid chloride introduces a thioacyl group ($M=Y$—CS—). Reaction with a substituted alkyl or aryl sulfonyl chloride introduce a Y—$SO_2$— group. For example reaction with naphthyl sulfonyl chloride would give the Y—$SO_2$— derivative where Y was a naphthyl group. Reaction with a substituted alkyl or aryl chloroformate introduces a Y—O—CO— group. Reaction with a substituted alkyl or aryl chlorothioformate introduces a Y—O—CS—. There are many alternate reaction schemes that can be used to introduce all of the above M-groups to give either M-$AA^2$-OH or M-$AA^2$-OR'.

The M-$AA^2$-OH derivatives can then be used directly to synthesize ketoamide using various synthetic methods or can be converted into the dipeptides M-$AA^2$-$AA^1$-OH, which can then be used in the Dakin-West reaction. The substituted dipeptides M-$AA^2$-$AA^1$-OH can also be prepared directly from H-$AA^2$-$AA^1$-OH using the reactions described above for introduction of the M-group. Alternately, the M-group can be introduced by reaction with carboxyl blocked peptides to give M-AA²-AA¹-OR', followed by the removal of the blocking group R'. The techniques for introduction of the M-group into amino acids and peptide is well documented in The Peptides, Houben-Weyl, and many other textbooks on organic synthesis.

The M-group can also be introduced by first synthesizing a Z-blocked dipeptide ketoamide, deblocking the Z group from final ketoamide product, and then reaction with an appropriate acylating or sulfonylation agent. An example of this strategy is shown in Scheme 2.

Scheme 2. Introduction of the M-group directly into dipeptide ketoamides.

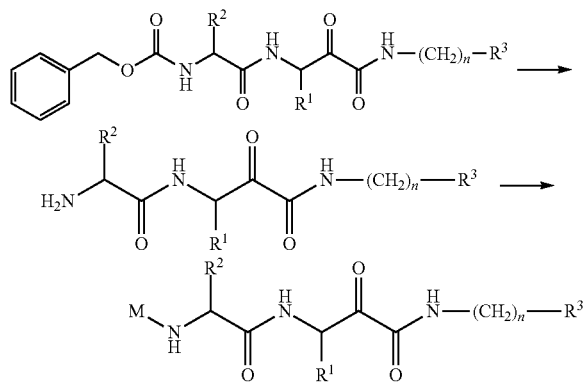

When the M-group is a morpholinocarbonyl group (Mu=O (CH₂CH₂)₂N—CO—) or a similar structure, the synthesis can involve an isocyanate derivative of the amino acid ester. Scheme 3 shows this synthetic scheme. An amino acid methyl ester or benzyl ester isocyanate, which can be synthesized from the corresponding amino acid hydrochloride salt according to the procedure by Nowick et al., is dissolved in CH₂Cl₂ and cooled down to 0° C. (*J. Org. Chem.* 57:7364-6, 1992, which is incorporated by reference herein in its entirety). Morpholine is added to the stirred solution of amino acid methyl ester or benzyl ester isocyanate. The reaction mixture is stirred vigorously for about 16 hours at room temperature. The solvent is removed and purification on a silica gel column chromatography gives the desired product. The methyl ester or the benzyl ester of the product is hydrolyzed and then reacted with the corresponding amino acid methyl ester or benzyl ester using standard peptide coupling reactions. Deprotection of the methyl or benzyl ester gives the corresponding peptide acid.

Scheme 3. General procedure for the introduction of a morphinocarbonyl group as M-CO-into a dipeptide precursor.

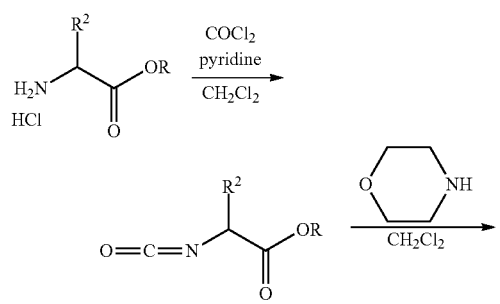

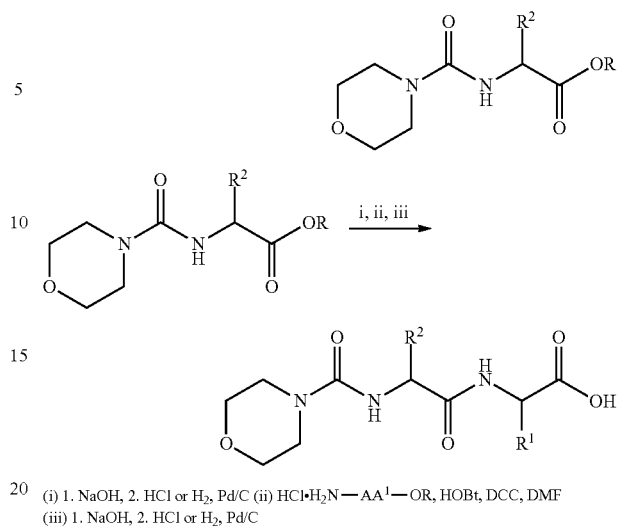

(i) 1. NaOH, 2. HCl or H₂, Pd/C (ii) HCl·H₂N—AA¹—OR, HOBt, DCC, DMF
(iii) 1. NaOH, 2. HCl or H₂, Pd/C

2. Synthesis of Peptide Ketoesters and Ketoacids

The α-ketoamide inhibitors can be prepared from the corresponding dipeptide α-ketoesters or α-ketoacids. The α-ketoester can be prepared by a two step Dakin-West reaction from the corresponding dipeptide acid (M-AA²-AA¹-OH) as shown in Scheme 4 (Charles et al., *J. Chem. Soc. Perkin 1*, 1139-1146, 1980, which is incorporated by reference herein in its entirety).

Scheme 4. Procedure for the synthesis of dipeptide ketoesters and ketoacids via a Dakin-West reaction.
The dipeptide acid 3a is Z-Leu-Abu-OH and 3b is Z-Leu-Phe-OH.

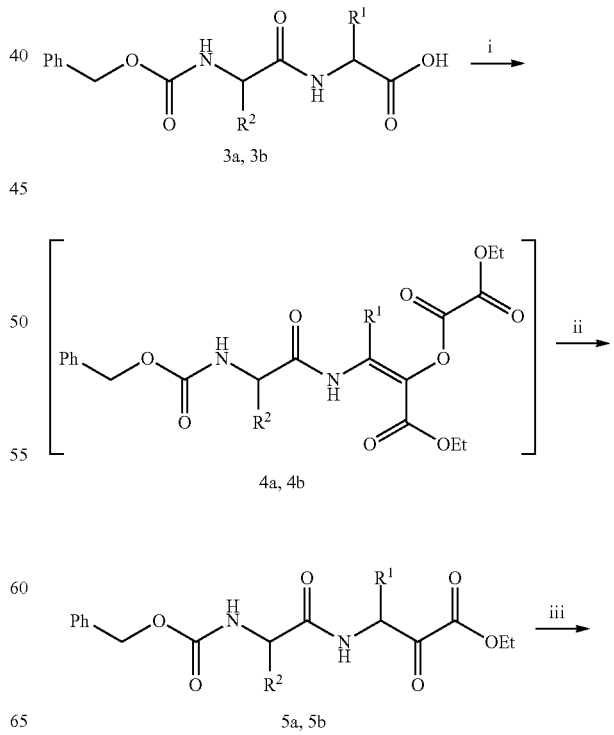

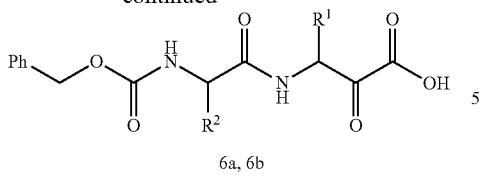

6a, 6b i) DMAP, Pyridine, EtOCOCOCl/THF. ii) NEt₃/EtOH. iii) NaOH/MeOH.

The R group in the ketoester structures can be introduced during the Dakin-West reaction by reaction with an oxalyl chloride Cl—CO—CO—O—R. In Scheme 4, it is ethyl.

There are numerous other methods for the synthesis of dipeptide ketoesters, ketoacids, and ketoamides. These synthetic methods have been reviewed by Chu and Powers, "Peptide α-Oxo Esters, α-Oxo Acids, and α-Oxoamides," In Houben-Weyl Methods of Organic Chemistry. Synthesis of Peptides and Peptidomimetics, Goodman et al., Eds., Georg Thieme Verlag, Stuttgart and New York, Vol. E 22d, 2003, pp. 244-55, which is incorporated by reference herein.

3. Synthesis of Precursor Amines

A first general procedure for the synthesis of the precursor amines involves the reaction of secondary amines with dihaloalkanes to add the linker by a single alkylation reaction. The second halogen on the linker can then be reacted with sodium azide to obtain the corresponding azide derivatives. The catalytic reduction of the azides in the presence of palladium activated on carbon and hydrogen gas gives the precursor amines (Scheme 5).

Scheme 5. General procedure for the synthesis of precursor amines via a dihaloalkane.

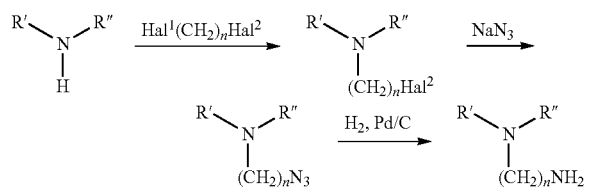

A second general procedure involves reaction of secondary amines with acrylonitrile to attach the linker on the amine. Then catalytic reduction of the nitriles with palladium activated on carbon and hydrogen gas gives the desired precursor amines (Scheme 6).

Scheme 6. General procedure for the synthesis of precursor amines via reaction with acrylonitrile.

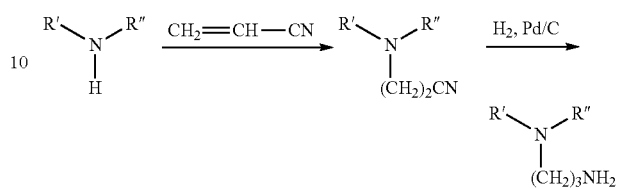

Some precursor amines are commercially available including 2-dimethylaminopropylamine and dimethylaminoethylamine. These compounds are available from Acros Organics and Aldrich.

4. Synthesis of Ketoamide Products

Ketoamides M-AA²-AA¹-CONHR can be prepared indirectly from the ketoesters. The ketone carbonyl group can be first protected as shown in Scheme 7 and then the ketoamide can be prepared by reaction with an amine (RNH₂). The product can be easily isolated from the reaction mixture when using this procedure. This procedure will also work with other ketone protecting groups.

Scheme 7. Synthesis of ketoamides from blocked ketoesters.

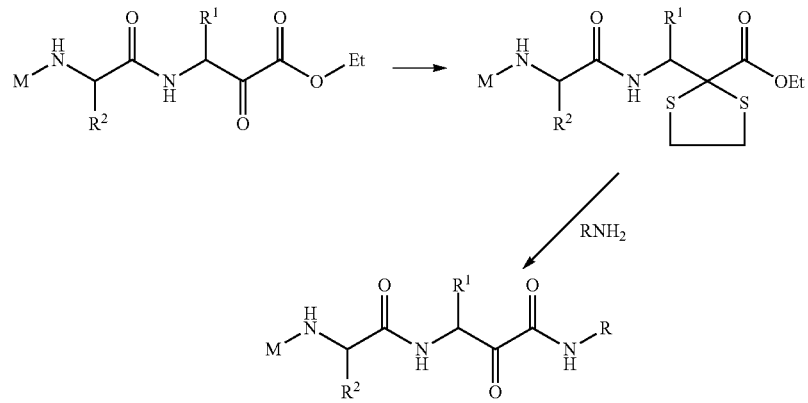

Another synthetic procedure involves use of the ketoacid obtained by hydrolysis of the corresponding ketoester. The ketoacid can be used as a precursor to the α-ketoamide via coupling with an amine (RNH₂) using standard peptide coupling reagents, which results in formation of the peptide α-ketoamide (Scheme 8).

Scheme 8. Synthesis of ketoamides from ketoacids.

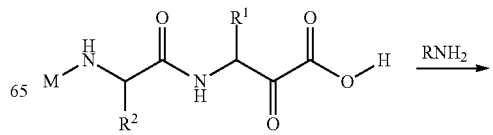

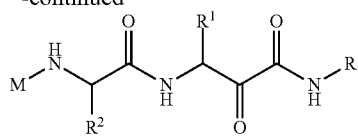

Pharmaceutical Compositions and Methods of Use

Also disclosed herein are pharmaceutical compositions that comprise a compound according to Formula I and a pharmaceutically accepted carrier, diluent, or excipient. Accordingly, the compounds of Formula I can be used in the manufacture of a medicament. Pharmaceutical compositions can also include thickeners, buffers, preservatives, surface active agents and the like in addition to the compounds disclosed herein. Pharmaceutical compositions can also include one or more additional active ingredients such as antimicrobial agents, anti-inflammatory agents, anesthetics, and the like. In one specific example, the disclosed pharmaceutical compositions can comprise a compound according to Formula I and a pharmaceutically acceptable carrier and an antihyperproliferative agent Pharmaceutical carriers are known to those skilled in the art. These most typically would be standard carriers for administration of drugs to humans, including solutions such as sterile water, saline, and buffered solutions at physiological pH. Suitable carriers and their formulations are described in Remington: The Science and Practice of Pharmacy, 21st Ed., Lippincott Williams & Wilkins, Philadelphia, Pa., 2005, which is incorporated by reference herein for its teachings of carriers and pharmaceutical formulations. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution can be from about 5 to about 8 (e.g., from about 7 to about 7.5). Further carriers include sustained release preparations such as semipermeable matrices of solid hydrophobic polymers containing the disclosed compounds, which matrices are in the form of shaped articles, e.g., films, liposomes, microparticles, or microcapsules. It will be apparent to those persons skilled in the art that certain carriers can be more preferable depending upon, for instance, the route of administration and concentration of composition being administered. Other compounds can be administered according to standard procedures used by those skilled in the art.

The disclosed pharmaceutical formulations can be used therapeutically or prophylactically. They can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection, intrasternal injection, or infusion techniques. The disclosed compounds can be administered intravenously, intraperitoneally, intramuscularly, subcutaneously, intracavity, or transdermally. The dosage depends primarily on the specific formulation and on the object of the therapy or prophylaxis. The amount of the individual doses as well as the administration is best determined by individually assessing each case.

The pharmaceutical compositions containing the active ingredient can be in a form suitable for oral use, for example, as tablets, troches, lozenges, aqueous or oily suspensions, dispersible powders or granules, emulsions, hard or soft capsules, syrups, or elixirs. Dosage levels of the order of 0.2 mg to 140 mg per kilogram of body weight per day are useful in the treatment of the above-indicated conditions (10 mg to 7 gm per patient per day). The amount of active ingredient that may be combined with carrier materials to produce a single dosage form will vary depending upon the host treated and the particular mode of administration.

For injection, the therapeutic amount of the peptide ketoamides or their pharmaceutically acceptable salts, derivatives or prodrugs will normally be in the dosage range from 0.2 to 140 mg/kg of body weight. Administration is made by intravenous, intramuscular, or subcutaneous injection. Accordingly, pharmaceutical compositions for parenteral administration will contain from about 10 mg to 7 gm of the compounds per dose. In addition to the active ingredient, these pharmaceutical compositions will usually contain a buffer, e.g. a phosphate buffer which keeps the pH in the range from 3.5 to 7 and sodium chloride, mannitol, or sorbitol for adjusting the isotonic pressure.

A composition for topical application can be formulated as an aqueous solution, lotion, jelly or an oily solution or suspension, ointments, creams, gels, drops, suppositories, sprays, liquids and powders. Conventional pharmaceutical carriers, aqueous, powder or oily bases, thickeners and the like can be desirable. A composition in the form of an aqueous solution is obtained by dissolving the compounds disclosed herein in aqueous buffer solution of pH 4 to 6.5 and, if desired, adding a polymeric binder. An oily formulation for topical application is obtained by suspending the compounds disclosed herein in an oil, optionally with the addition of a swelling agent such as aluminium stearate and/or a surfactant.

Preparations for parenteral administration include sterile aqueous or non-aqueous solutions, suspensions, and emulsions. Examples of non-aqueous solvents are propylene glycol, polyethylene glycol, vegetable oils such as olive oil, marine oils, and injectable organic esters such as ethyl oleate. Aqueous carriers include water, alcoholic/aqueous solutions, and emulsions or suspensions, including saline and buffered media. Parenteral vehicles include sodium chloride solution, Ringer's dextrose, dextrose and sodium chloride, lactated Ringer's, and fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the formulations can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The disclosed compounds and compositions can be used to treat a pathology, in particular a neural pathology such as nerve degeneration. The nerve degeneration can be related to diabetes or neurotoxic agents. One example provides a method for treating a neurodegenerative disease by administering to a patient a therapeutically effective amount of a compound of the Formula I. Examples of such neurodegenerative disorders are stroke, Alzheimer's disease, Parkinson's disease, multiple sclerosis, neuropathies, Huntington's disease, dentatorubropallidoluysian atrophy, spinocerebellar atrophy type 3, spinal bulbar muscular atrophy, and myotrophic lateral sclerosis.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, pH, etc.) but some errors and deviations should be accounted for. Unless indicated otherwise, parts are parts by weight, temperature is in ° C. or is at ambient temperature, and pressure is at or near atmospheric. There are numerous variations and combinations of conditions, e.g., component concentrations, temperatures, pressures, and other reaction ranges and conditions that can be used to optimize the product purity and yield obtained from the described process. Only reasonable and routine experimentation will be required to optimize such process conditions.

Certain materials, compounds, compositions, and components disclosed herein can be obtained commercially or readily synthesized using techniques generally known to those of skill in the art. For example, the starting materials and reagents used in preparing the disclosed compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplements (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Example 1

Synthesis of Morpholinocarbonyl-Alanylalanine (Mu-Ala-Ala-OH)

Alanine methyl ester isocyanate, which was synthesized from the corresponding amino acid hydrochloride salt according to the procedure by Nowick et al., was dissolved in $CH_2Cl_2$ and cooled down to 0° C. Morpholine was added to the stirred solution of alanine methyl ester isocyanate. The reaction mixture was stirred vigorously for 16 hours at room temperature. After removal of solvent, the crude product was purified by a silica gel column chromatography. The methyl ester group of Mu-Ala-$OCH_3$ was hydrolyzed in MeOH using NaOH (1 M aqueous, 1.1 eq) under standard deblocking conditions. Mu-Ala-OH was then coupled to alanine methyl ester hydrochloride (HCl.$NH_2$-Ala-$OCH_3$) using the DCC/HOBt coupling method. To a stirred solution of the Mu-Ala-OH (1 eq) in DMF at −15° C., HOBt (1.5 eq) was added. The hydrochloride salt of the alanine methyl ester was pretreated with NMM (1.5 eq) at −15° C. DMF prior to addition. DCC (1.5 eq) was added to the solution and the reaction mixture was allowed to react for 16 hours at room temperature. The DMF was evaporated, and the residue was redissolved in EtOAc. The organic layer was washed with 2% citric acid, saturated $NaHCO_3$, saturated NaCl, dried over $MgSO_4$, and concentrated. Purification on a silica gel column with the proper eluant gave the compound Mu-Ala-Ala-$OCH_3$. This compound was then hydrolyzed in MeOH using NaOH (1 M aqueous, 1.1 eq) under standard deblocking conditions to give the Mu-Ala-Ala-OH, the dipeptide acid precursor (Mu=O$(CH_2CH_2)_2$N—CO—). This procedure is illustrated in Scheme 9.

Scheme 9. Specific procedure for the synthesis of of morpholinocarbonyl-alanylalanine (Mu-Ala-Ala-OH).

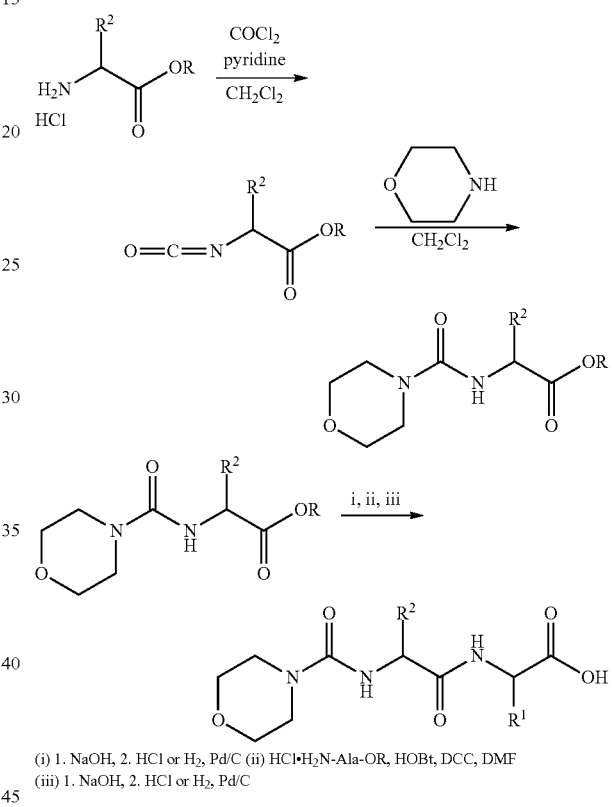

(i) 1. NaOH, 2. HCl or $H_2$, Pd/C (ii) HCl•$H_2$N-Ala-OR, HOBt, DCC, DMF
(iii) 1. NaOH, 2. HCl or $H_2$, Pd/C Example 2

Synthesis of N-Cbz-Leu-Abu-COOEt and N-Cbz-Leu-Phe-COOEt (5a and 5b from Scheme 4)

The general experimental conditions for the Dakin-West acylation and the hydrolysis reaction are given in this procedure. These general reactions are also discussed above and are shown in Scheme 4. The quantities of the reagents, reaction times, and the product yields are listed in Table 2. To 50 mL of THF, 0.02 mole (1 equivalent) of the dipeptide acid (3a or 3b in Scheme 4), 4-dimethylaminopyridine (DMAP), pyridine, and ethyl oxalyl chloride were added sequentially. The resulting mixture was stirred at reflux temperature for 2 to 6 hours. After removing the heat source, 1 M HCl (50 mL) was added to the brown solution. The mixture was extracted with ethyl acetate (2×100 mL). The combined extract was washed with 100 mL of saturated NaCl, dried over $MgSO_4$ overnight, and filtered. Ethyl acetate was removed from the filtrate to give a mixture of products containing the dipeptidyl enol ester (4a or 4b in Scheme 4), as identified by MS (FAB mode): 4a, thin layer chromatography (TLC, solvent A) $R_f$=0.65; MS (calculated for M+1, $C_{25}H_{35}N_2O_9$, 507) m/e 507; 4b, TLC (solvent A) $R_f$=0.53; MS (calculated for M+1, $C_{30}H_{37}N_2O_9$, 569) m/e 569. The mixture of products was dissolved in 20 mL of absolute ethanol and stirred in an ice bath. Triethylamine (2.8 mL, 1 equivalent) was added in one portion and stirring was continued for 1-4 hours at room temperature. Solvent was removed from the final mixture using a rotary evaporator. The crude oil was subjected to column chromatography to give 8.8-15.0 mmol (44-76%) of the dipeptidyl α-keto ester (5a or 5b in Scheme 4) as a light yellow oil: 5a, TLC (solvent A) $R_f$=0.37; $^1$H NMR (CDCl$_3$) δ=0.86-0.93 (m, 9H), 1.26-1.37 (m, 4H), 1.49-1.70 (m, 4H), 1.91-1.98 (m, 1H), 4.23-4.38 (m, 2H), 5.03-5.13 (m, 3H), 5.67-5.73 (m, 1H), 7.21-7.32 (m, 6H); HRMS (calculated for M+1, $C_{12}H_{31}N_2O_6$, 407.2182) m/e 407.2178; 5b, TLC (solvent A) $R_f$=0.31; $^1$H NMR (CDCl$_3$) δ=0.70-0.76 (m, 1H), 0.79-0.90 (m, 6H), 1.22-1.61 (m, 5H), 2.93-3.07 (m, 1H), 3.19-3.28 (m, 1H), 4.14-4.33 (m, 3H), 5.08 (dd, 14.25, 12.60, 12.30 Hz, 2H), 5.23-5.43 (m, 2H), 6.77-6.84 (m, 1H), 7.12-7.29 (m, 5H), 7.33 (s, 5H); HRMS (calculated for M+1, $C_{26}H_{33}N_2O_6$, 469.2339) m/e 469.2337.

TABLE 2

Dakin-West Acylation and Hydrolysis Reaction Conditions.

| Entry No. | Dipeptide Acid | DMAP[a] | Pyridine[a] | Ethyl Oxalyl Chloride[a] | Reflux Time | Hydrolysis Time | Product (Yield)[b] |
|---|---|---|---|---|---|---|---|
| 1 | 3a | 0.03 eq | 3 eq | 2.1 eq | 4 hr | 1 hr | 5a (58%) |
| 2 | 3a | 0.05 eq | 3 eq | 2.1 eq | 4 hr | 1 hr | 5a (76%) |
| 3 | 3a | 0.05 eq | 4 eq | 2.1 eq | 6 hr | 1 hr | 5a (75%) |
| 4 | 3a | 0.10 eq | 4 eq | 2.1 eq | 6 hr | 1 hr | 5a (68%) |
| 5 | 3b | 0.00 eq | 4 eq | 2.1 eq | 4 hr | 1 hr | 5b (50%) |
| 6 | 3b | 0.01 eq | 3 eq | 2.1 eq | 3 hr | 1 hr | 5b (48%) |
| 7 | 3b | 0.03 eq | 3 eq | 2.0 eq | 3 hr | 1 hr | 5b (58%) |
| 8 | 3b | 0.05 eq | 4 eq | 2.1 eq | 4 hr | 1 hr | 5b (68%) |
| 9 | 3b | 0.10 eq | 4 eq | 2.1 eq | 2 hr | 1 hr | 5b (53%) |
| 10 | 3b | 0.10 eq | 4 eq | 2.1 eq | 2 hr | 4 hr | 5b (56%) |
| 11 | 3b | 0.10 eq | 4 eq | 2.1 eq | 4 hr | 2 hr | 5b (55%) |
| 12 | 3b | 0.10 eq | 4 eq | 2.1 eq | 4 hr | 1 hr | 5b (56%) |
| 13 | 3b | 0.10 eq | 4 eq | 2.1 eq | 5 hr | 1 hr | 5b (68%) |
| 14 | 3b | 0.10 eq | 4 eq | 2.1 eq | 6 hr | 1 hr | 5b (62%) |
| 15 | 3b | 0.10 eq | 3 eq | 2.1 eq | 5 hr | 1 hr | 5b (56%) |
| 16 | 3b | 0.10 eq | 5 eq | 2.1 eq | 5 hr | 1 hr | 5b (62%) |
| 17 | 3b | 0.20 eq | 4 eq | 2.1 eq | 5 hr | 1 hr | 5b (66%) |
| 18 | 3b | 0.20 eq | 4 eq | 3.1 eq | 5 hr | 2 hr[c] | 5b (44%) |

[a]Expressed in molar equivalents relative to the dipeptide acid used.
[b]Expressed in molar percent yield relative to the dipeptide acid used.
[c]Two molar equivalents of triethyl amine were required to complete the hydrolysis reaction. The dipeptide ketoester 5a is Z-Leu-Abu-CO-OEt, and 5b is Z-Leu-Phe-CO-OEt (all compound numbers refer to Scheme 4).

Example 3

Synthesis of N-Cbz-Leu-Abu-COOH (6a)

To a mixture of 5.45 g (0.013 mole) of 5a in 10 mL of methanol, 13 mL of 1 M NaOH solution was added in portions while stirring in an ice bath. The resulting mixture was stirred at room temperature for an hour and extracted with anhydrous ether (4×30 mL). The aqueous layer was acidified to pH 4 with 2 M HCl in an ice bath and extracted with Et$_2$O (2×50 mL). The combined ether extract was washed with saturated NaCl, dried over MgSO$_4$ overnight, and filtered. Ether was removed from the filtrate by evaporation and the product was dried under reduced pressure to give 3.64 g (0.0096 mole, 96%) of pale yellow hygroscopic flakes: $^1$H NMR (CDCl$_3$) δ=0.91 (d, 6.3 Hz, 9H), 1.47-1.75 (m, 5H), 1.93-1.97 (m, 1H), 4.35 (m, 1H), 5.04-5.13 (m, 3H), 5.82 (m, 1H), 7.32 (s, 5H); HRMS (calculated for M+1, $C_{19}H_{27}N_2O_6$, 379.1869) m/e 379.1870.

Example 4

Synthesis of N-Cbz-Leu-Phe-COOH (6b)

The above hydrolysis conditions were followed using 5.25 g (0.011 mole) of 5b to give 4.33 g (0.0098 mole, 89%) of pale yellow hygroscopic flakes: $^1$H NMR (CDCl$_3$) δ=0.77-0.86 (m, 5H), 1.09-1.56 (m, 3H), 2.49-2.51 (m, 1H), 2.75-2.91 (m, 1H), 3.08-3.18 (m, 1H), 4.01-4.08 (m, 1H), 4.89-5.06 (m, 3H), 7.18-7.40 (m, 12H), 8.49 (t, 7.20, 7.20 Hz, 1H); HRMS (calculated for M+1, $C_{24}H_{29}N_2O_6$, 441.2026) m/e 441.2025.

Example 5

Synthesis of 9-(3-aminopropyl)adenine

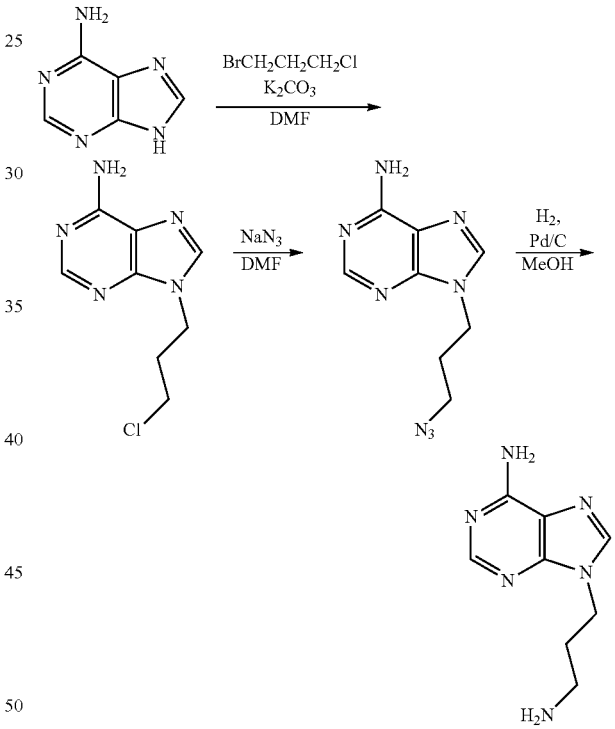

Scheme 10. Procedure for the synthesis of 9-(3-aminopropyl)adenine.

A mixture of adenine, 1-bromo-3-chloropropane, and potassium carbonate in DMF was stirred at room temperature under argon for 4 days, filtered and evaporated to dryness. The crude product was washed with water and dried. Recrystallization from ethanol gave 9-(3-chloropropyl)adenine.

A mixture of 9-(3-chloropropyl)adenine and sodium azide in DMF was stirred at 80° C. for 24 hours, cooled to room temperature and filtered. The solid was washed with CH$_2$Cl$_2$. The solvent was removed from the combined filtrates and the residue was taken up in water with sonication. The aqueous layer was extracted with CH$_2$Cl$_2$. After removing the solvent, the crude product was recrystallized from ethanol to give 9-(3-azidopropyl)adenine as a white crystalline solid.

A mixture of 9-(3-azidopropyl)adenine and 5% palladium on carbon in methanol was reacted with hydrogen gas at room temperature for 22 hours. The catalyst was removed by filtration, the solvent was removed to give 9-(3-aminopropyl)adenine as a white solid. The reference for the synthetic procedure is Zhang et al., "Syntheses and coordination chemistry of aminomethylphosphine derivatives of adenine," *Euro. J. Inorg. Chem.* 13:2426-37, 2003, which is incorporated by reference herein in its entirety.

Example 6

Synthesis of 1-(3-aminopropyl)cytosine

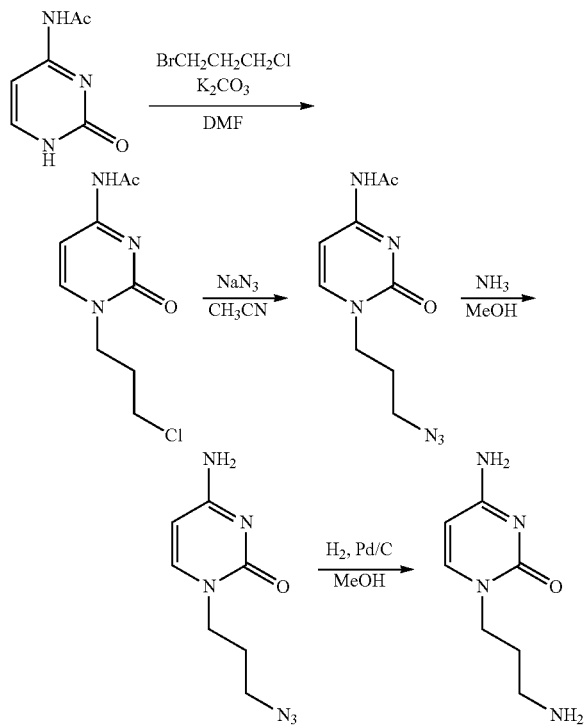

A mixture of N-acetylcytosine, 1-bromo-3-chloropropane, and potassium carbonate in DMF was stirred at room temperature under argon for 4 days, filtered and evaporated to dryness. The crude product was purified by column chromatography and gave 1-(3-chloropropyl)-$N^4$-acetylcytosine.

A mixture of 1-(3-chloropropyl)-$N^4$-acetylcytosine and sodium azide in acetonitrile was refluxed for 24 hours, cooled to room temperature, and filtered. The crude product was purified by silica gel column chromatography and gave 1-(3-azidopropyl)-$N^4$-acetylcytosine as a white solid.

A mixture of 1-(3-azidopropyl)-$N^4$-acetylcytosine was reacted with 7N ammonia solution in methanol at room temperature for 2 days to give 1-(3-azidopropyl)cytosine as a white solid.

A mixture of 1-(3-azidopropyl)cytosine and 5% palladium on carbon in methanol was reacted with hydrogen gas at room temperature for 8 h. The catalyst was removed by filtration, the solvent was removed to give 1-(3-aminopropyl)cytosine as a white solid. The references for this synthesis are Zhang et al. "Syntheses and coordination chemistry of aminomethylphosphine derivatives of adenine," *Euro. J. Inorg. Chem.* 13:2426-37, 2003; Summers et al., "Synthesis of Fluorescent Labeled Derivatives of Aminopropylpyrimidines," *J. Org. Chem.* 40(11): 1559-61, 1975; and Lafitte et al., "Quadruply hydrogen bonded cytosine modules for supramolecular applications," *J. Am. Chem. Soc.* 128(20):6544-5, 2006, each of which are incorporated by reference herein in their entireties.

Example 7

Synthesis of 1-(3-aminopropyl)-4-methylpiperazine

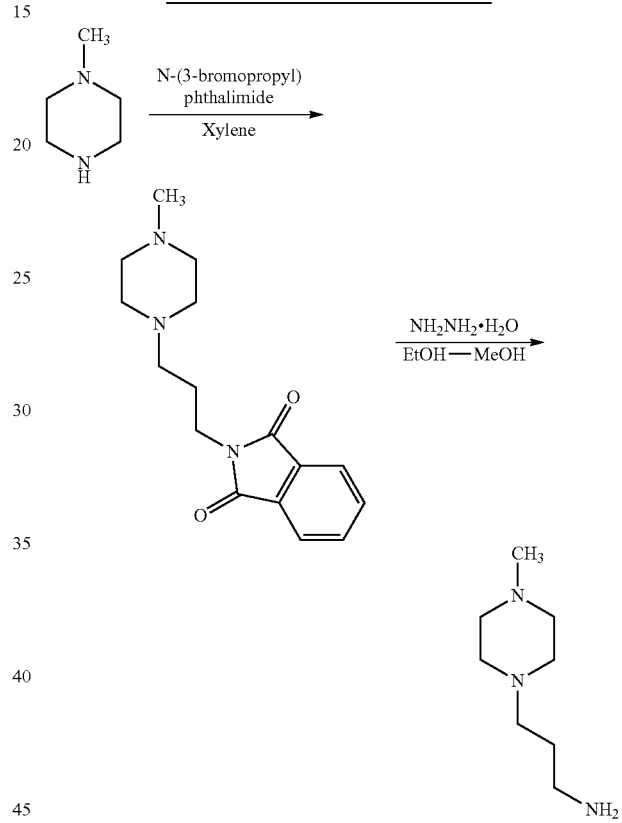

A solution of N-(3-bromopropyl)phthalimide in xylene was added dropwise to a solution of 1-methylpiperazine in xylene at 70° C. After addition was complete, the mixture was heated under reflux for 20 hours. A precipitate was removed by filtration and the filtrate was concentrated. The crude product was purified by silica gel column chromatography to give the product N-(3-(4-methylpiperazin-1-yl)propyl)phthalimide as an oil.

A solution of N-(3-(4-methylpiperazin-1-yl)propyl)phthalimide and hydrazine monohydrate in ethanol and methanol was refluxed for 4 hours. After cooling to room temperature, concentrated HCl was added and the mixture heated under reflux for another hour. After removing the solvent, water was added, the mixture stirred, and insoluble material removed by filtration. Solid $K_2CO_3$ and $CH_2Cl_2$ were added to the aqueous layer, the mixture stirred, and was then filtered. The organic layer was washed with water. The combined aqueous layers were washed with $Et_2O$. Water was removed from the organic layers, they were then dried and evaporated to give 1-(3-aminopropyl)-4-methylpiperazine as an oil. A reference for this synthesis is Hou et al., "Efficient syntheses of oncinotine and neooncinotine," *J. Org. Chem.* 69(18):6094-9, 2004, which is incorporated by reference herein.

Nucleotide bases with substituents can be synthesized by similar procedures starting from the appropriate nucleotide base. For example, the 2-methoxy derivative of adenine can be synthesized via the procedure shown in FIG. 14. Introduction of a 2-methoxy group on the adenine ring would involve reaction of 2-chloroadenine with sodium methoxide to produce 2-methoxyadenine. Then the same reaction scheme as shown in Scheme 10 can be used to attach the spacer onto the 9-position of the 2-methoxyadenine.

Scheme 13. Procedure for the synthesis of 9-(3-aminopropyl)-2-methoxyadenine.

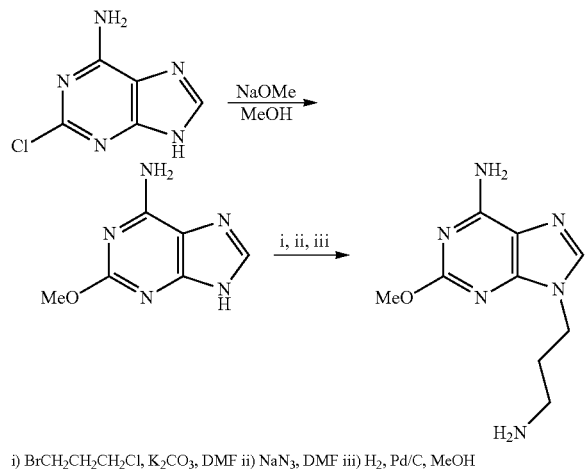

i) BrCH$_2$CH$_2$CH$_2$Cl, K$_2$CO$_3$, DMF ii) NaN$_3$, DMF iii) H$_2$, Pd/C, MeOH Example 8

Synthesis of 3-(Benzyloxycarbonyl-L-leucylamino)-N-(3-(6-amino-9H-purin-9-yl)propyl)-2-oxopentanamide (Z-Leu-Abu-CONH—(CH$_2$)$_3$-adenin-9-yl)

A mixture of adenine (4.05 g, 30 mM), 1-bromo-3-chloropropane (21.3 g, 13.4 mM), and potassium carbonate (10.4 g, 75 mM) in DMF (200 mL) was stirred at room temperature under argon for 4 days, filtrated, and evaporated to dryness. The crude product was washed with water and dried. Recrystallization from ethanol gave 9-(3-chloropropyl)adenine in 59% yield.

A mixture of 9-(3-chloropropyl)adenine (1.9 g, 9 mM) and sodium azide (1.75 g, 27 mM) in DMF was stirred at 80° C. for 24 hours, cooled to room temperature, and filtered. The solid was washed with CH$_2$Cl$_2$. The solvent was removed from the combined filtrates and the residue was taken up in water with sonication. The aqueous layer was extracted with CH$_2$Cl$_2$ (3×60 mL). After removing solvent, the crude product was recrystallized from ethanol to give 9-(3-azidopropyl)adenine as a white crystalline solid in 81% yield.

A mixture of 9-(3-azidopropyl)adenine (0.5 g, 2.3 mM) and 5% palladium on carbon (0.5 g) in methanol was reacted with hydrogen gas at room temperature for 22 hours. The catalyst was removed by filtration, the solvent removed to give 9-(3-aminopropyl)adenine as a white solid in 76% yield. $^1$H NMR (DMSO-d$_6$): δ=1.80 (m, 2H, CH$_2$), 2.45 (m, 2H, CH$_2$), 3.35 (S, 2H, NH$_2$), 4.20 (m, 2H, CH$_2$), 7.20 (s, 2H, NH$_2$), 8.10 (s, 2H, CH). MS (ED+): 193.0.

The ketoamide product Z-Leu-Abu-CONH—(CH$_2$)$_3$-adenin-9-yl was obtained from 9-(3-aminopropyl)adenine and the ketoacid Z-Leu-Abu-COOH (30) using the EDC/HOBt coupling method, purified by column chromatography on silica gel with 85:15 CH$_2$Cl$_2$:MeOH as the eluant, then recrystallization from CH$_3$COOEt/hexane to give a white solid (27% yield). $^1$H NMR (CDCl$_3$): δ=0.91 (m, 9H, CH$_3$ of Val and Abu), 1.60-1.80 (m, 5H, CH$_2$ and CH of Leu and Abu), 2.00 (m, 2H, CH$_2$), 3.20 (2H, CH$_2$), 4.24 (m, 3H, CH$_2$ and α-H), 5.11 (s, 2H, Z), 5.20 (m, 1H, α-H), 6.20 (s, 1H, NH), 6.80 (b, 1H, NH), 7.20-7.40 (m, 6H, Ph and NH), 7.85 (d, 1H, CH of adenine), 8.36 (d, 111, CH of adenine). HRMS (FAB) for C$_{27}$H$_{37}$N$_8$O$_5$: m/z 553.2856, calcd. 553.2881.

Example 9

Synthesis of 3-(Benzyloxycarbonyl-L-leucylamino)-N-(3-(4-methylpiperazin-1-yl)propyl)-2-oxopentanamide (Z-Leu-Abu-CONH—(CH$_2$)$_3$-(4-methylpiperazin-1-yl)

A solution of N-(3-bromopropyl)phthalimide (8.04 g, 30 mM) in xylene (60 mL) was added dropwise to a solution of 1-methylpiperazine (6.61 g, 66 mM) in xylene (90 mL) at 70° C. After the addition was complete, the mixture was heated under reflux for 20 hours. A precipitate was removed by filtration and the filtrate was concentrated. The crude product was purified by silica gel chromatography with 9:1 CH$_2$Cl$_2$:MeOH to give the product N-(3-(4-methylpiperazin-1-yl)propyl)phthalimide as an oil in 72% yield.

A solution of N-(3-(4-methylpiperazin-1-yl)propyl)phthalimide (6.2 g, 21.6 mM) and hydrazine monohydrate (1.13 g, 26 mM) in ethanol (60 mL) and methanol (60 mL) was refluxed for 4 hours. After cooling to room temperature, concentrated HCl (2.4 mL) was added and the mixture heated under reflux for another hour. After removing the solvent, water (100 mL) was added, the mixture stirred and insoluble material removed by filtration. Solid K$_2$CO$_3$ (1.2 eq) and CH$_2$Cl$_2$ (100 mL) was added to the aqueous layer; the mixture stirred, and was then filtered. The organic layer was washed with water (3×20 mL). The combined aqueous layers were washed with Et$_2$O. Water was removed from the organic layers, which were then dried and evaporated to give 1-(3-aminopropyl)-4-methylpiperazine as an oil in 39% yield. $^1$H NMR (CDCl$_3$): δ=1.55 (m, 2H, CH$_2$), 2.20 (s, 3H, CH$_3$), 2.34 (t, 2H, CH$_2$), 2.67 (t, 2H, CH$_2$). MS (ES+): 157.9.

The ketoamide Z-Leu-Abu-CONH—(CH$_2$)$_3$-(4-methylpiperazin-1-yl) was synthesized from 1-(3-aminopropyl)-4-methylpiperazine and Z-Leu-Abu-COOH (30) using the EDC/HOBt coupling method, purified twice by column chromatography on silica gel using 80:20 CH$_2$Cl$_2$:MeOH and 85:15 CH$_2$Cl$_2$:MeOH as the eluant to give a yellow semisolid in 16% yield. $^1$H NMR (CDCl$_3$): δ=0.91 (m, 9H, CH$_3$ of Val and Abu), 1.60-1.80 (m, 5H, CH$_2$ and CH), 2.00 (m, 2H, CH$_2$), 2.44 (s, 3H, CH$_3$ of piperazine), 2.50-2.65 (m, 8H, CH$_2$ of piperazine), 3.30 (m, 2H, CH$_2$), 4.20 (m, 3H, CH$_2$ and α-H), 5.10 (s, 2H, Z), 5.15 (m, 1H, α-H), 6.70 (b, 1H, NH), 7.20-7.30 (m, 6H, Ph and NH), 8.60 (b, 1H, NH). HRMS (FAB) for C$_{27}$H$_{44}$N$_5$O$_5$: m/z 518.3301.

Example 10

Synthesis of Z-Leu-Abu-CONH—(CH$_2$)$_3$—N(CH$_3$)$_2$

The dipeptide ketoamide was obtained from the blocked derivative Z-Leu-NHCH(C$_2$H$_5$)C(—S(CH$_2$)$_2$S—)CO—OEt and $(CH_3)_2N(CH_2)_3NH_2$ in THF at room temperature for 12 hours. Purification by column chromatography twice on silica gel with 80:20 $CH_2Cl_2$:MeOH and 85:15 $CH_2Cl_2$:MeOH as the eluant provided a yellow semi-solid in 11% yield. $^1H$ NMR ($CDCl_3$): δ=0.91 (m, 9H, $CH_3$ of Val and Abu), 1.50-1.70 (m, 5H, $CH_2$ and CH), 2.00 (m, 2H, $CH_2$), 2.70 (s, 6H, $CH_3$), 3.40 (m, 2H, $CH_2$), 4.20 (m, 2H, $CH_2$), 4.30 (b, 1H, α-H), 5.10 (s, 2H, Z), 5.40 (m, 1H, α-H), 6.40 (b, 1H, NH), 7.20-7.30 (m, 6H, Ph and NH), 7.80 (b, 1H, NH). HRMS (FAB) for $C_{24}H_{39}N_4O_5$: m/z 463.2973.

Example 11

Z-Leu-Phe-CONH—$(CH_2)_3$—$N(CH_3)_2$

The dipeptide ketoamide was obtained from Z-Leu-Phe-COOH and $(CH_3)_2N(CH_2)_3NH_2$ using the EDC/HOBt coupling method. Purification by column chromatography twice on silica gel with 80:20 $CH_2Cl_2$:MeOH as the eluant, then by TLC, provided a yellow semi-solid, in 10% yield. $^1H$ NMR ($CDCl_3$): δ=0.84 (m, 6H, $CH_3$ of Val), 1.50-1.80 (m, 5H, $CH_2$ and CH), 2.12 and 2.19 (d, 6H, $CH_3$), 3.00 (m, 2H, $CH_2$), 3.20 (m, 2H, $CH_2$), 4.15 (m, 2H, $CH_2$), 4.50 (b, 1H, α-H), 5.10 (m, 3H, Z and α-H), 6.82 (b, 1H, NH), 7.05-7.30 (m, 6H, Ph and NH), 7.40 (b, 1H, NH). HRMS (FAB) for $C_{29}H_{41}N_4O_5$: m/z 525.3077.

Example 12

Z-Leu-Phe-CONH—$(CH_2)_2$—$N(CH_3)_2$

The dipeptide ketoamide was obtained from Z-Leu-Phe-COOH and $(CH_3)_2N(CH_2)_2NH_2$ using the EDC/HOBt coupling method. Purification twice by column chromatography on silica gel with 80:20 $CH_2Cl_2$:MeOH as the eluant, and then by TLC, gave a yellow semi-solid in 7% yield. $^1H$ NMR ($CDCl_3$): δ=0.85 (m, 6H, $CH_3$ of Val), 1.50-1.70 (m, 3H, $CH_2$ and CH), 2.46 (s, 6H, $CH_3$), 3.00 (m, 2H, $CH_2$), 4.20 (m, 2H, $CH_2$), 4.31 (m, 2H, $CH_2$), 4.90 (b, 1H, α-H), 5.00 (m, 3H, Z and α-H), 6.20 (b, 1H, NH), 7.00-7.30 (m, 7H, Ph and NH). HRMS (FAB) for $C_{28}H_{39}N_4O_5$: m/z 511.3099.

Example 13

Z-Leu-Phe-CONH—$(CH_2)_3$-(4-methylpiperazin-1-yl)

The dipeptide ketoamide was obtained from Z-Leu-Phe-COOH and 1-methyl-4-(3-aminopropyl)piperazine using the EDC/HOBt coupling method. Purification twice by column chromatography on silica gel with 85:15 $CH_2Cl_2$:MeOH as the eluant gave a yellow semi-solid in 10% yield. $^1H$ NMR ($CDCl_3$): δ=0.81 (m, 6H, $CH_3$ of Val), 1.40-1.60 (m, 5H, $CH_2$ and CH), 2.28 (s, 6H, $CH_3$), 3.00 (m, 2H, $CH_2$), 3.20 (m, 2H, $CH_2$), 4.05 (m, 2H, $CH_2$), 4.50 (b, 1H, α-H), 5.02 (m, 3H, Z and α-H), 6.70 (b, 1H, NH), 7.05-7.30 (m, 7H, Ph and NH).

Example 14

Fluorimetric analysis of μI-II and m-calpain inhibition by Z-Leu-Abu-CONH—$(CH_2)_3$-adenin-9-yl, and Z-Leu-Abu-CONH—$(CH_2)_3$-(4-methylpiperazin-1-yl)

HEPES, heparin, and A23187 were obtained from Calbiochem. Suc-Leu-Tyr-AMC and chromogenic substrates were obtained from Sigma. Calpain I was purified from human erythrocytes according to the method of Kitahara (Kitahara et al., *J. Biochem.* 95:1759-66) omitting the Blue-Sepharose step. Calpain II from rabbit muscle and cathepsin B were purchased from Sigma. Papain was purchased from Calbiochem.

Assay of Inhibitory Potency.

Peptide α-ketoamides were assayed as reversible enzyme inhibitors. Various concentrations of inhibitors in $Me_2SO$ were added to the assay mixture, which contained buffer and substrate. The reaction was started by the addition of the enzyme and the hydrolysis rates were followed spectrophotometrically or fluorimetrically.

Calpain I from human erythrocytes and calpain II from rabbit were assayed using Suc-Leu-Tyr-AMC (Sasaki et al., *J. Biol. Chem.* 259:12489-94, 1984, which is incorporated by reference herein), and the AMC (7-amino-4-methylcoumarin) release was followed fluorimetrically (excitation at 380 nm, and emission at 460 nm). Calpains were assayed in 25 mM Tris pH=8.0, 10 mM $CaCl_2$. Fluorescence was followed using a Gilson FL-1A fluorometer or a Perkin-Elmer 203 Fluorescence spectrometer. Cathepsin B was assayed in 20 mM sodium acetate pH=5.2, 0.5 mM dithiothreitol using Bz-Phe-Val-Arg-p-nitroanilide as substrate. Alternately, cathepsin B was assayed with Z-Arg-Arg-AFC (Barrett and Kirschke, *Methods Enzymol.* 80:535-561, 1981, which is incorporated by reference herein), and the AFC (7-amino-4-trifluoromethylcoumarin) release was followed fluorimetrically (excitation at 400 nm and emission at 505 nm). Papain was assayed in 100 mM $KPO_4$, 1 mM EDTA, 2.5 mM cysteine pH=6.0 using Bz-Arg-AMC or Bz-Arg-NA (Kanaoka et al., *Chem. Pharm. Bull.* 25:3126-8, 1977, which is incorporated by reference herein) as a substrate. The AMC (7-amino-4-methylcoumarin) release was followed fluorimetrically (excitation at 380 nm, and emission at 460 nm). Enzymatic hydrolysis rates were measured at various substrate and inhibitor concentrations, and $K_I$ values were determined by either Lineweaver-Burk plots or Dixon plots.

A 50 mM Tris.HCl, 2 mM EDTA, 5 mM cysteine, pH 7.5 was used as a buffer for papain. A 88 mM $KH_2PO_4$, 12 mM $Na_2HPO_4$, 1.33 mM EDTA, 2.7 mM cysteine, pH 6.0 solution was used as a buffer for cathepsin B. A 20 mM Hepes, 10 mM $CaCl_2$, 10 mM mercaptoethanol, pH 7.2 buffer was utilized for calpain I and calpain II.

Enzymatic activity was monitored in real-time using a 1.5 mL quartz cuvette and a Perkin-Elmer LS50-B Luminescence Spectrophotometer. Duplicate assays were performed with 1.3 μM (EDANS)-EPLFAERK(SEQ ID NO:1)-(DABCYL) and 125 nM μI-II or m-calpain in a buffer solution containing 50 mM HEPES-HCl (pH 7.7) and 10 mM DTT. The reaction was initiated 420 seconds after mixing by the addition of 4 mM $CaCl_2$ and monitored at excitation and emission wavelengths of 335 nm and 500 nm, respectively. After a waiting period of 100 seconds, the inhibitor solution (either Z-Leu-Abu-CONH—$(CH_2)_3$-adenin-9-yl, or Z-Leu-Abu-CONH—$(CH_2)_3$-(4-methylpiperazin-1-yl) dissolved in DMSO) was added at a concentration of 1 μM (for the m-calpain assays) or 50 μM (for the μI-II assays). Control assays were performed by adding an equivalent volume of DMSO after the 100-second delay.

Evaluating the inhibitory potency of Z-Leu-Abu-CONH—$(CH_2)_3$-adenin-9-yl and Z-Leu-Abu-CONH—$(CH_2)_3$-(4-methylpiperazin-1-yl) on and m-calpain.

Figure 1B:
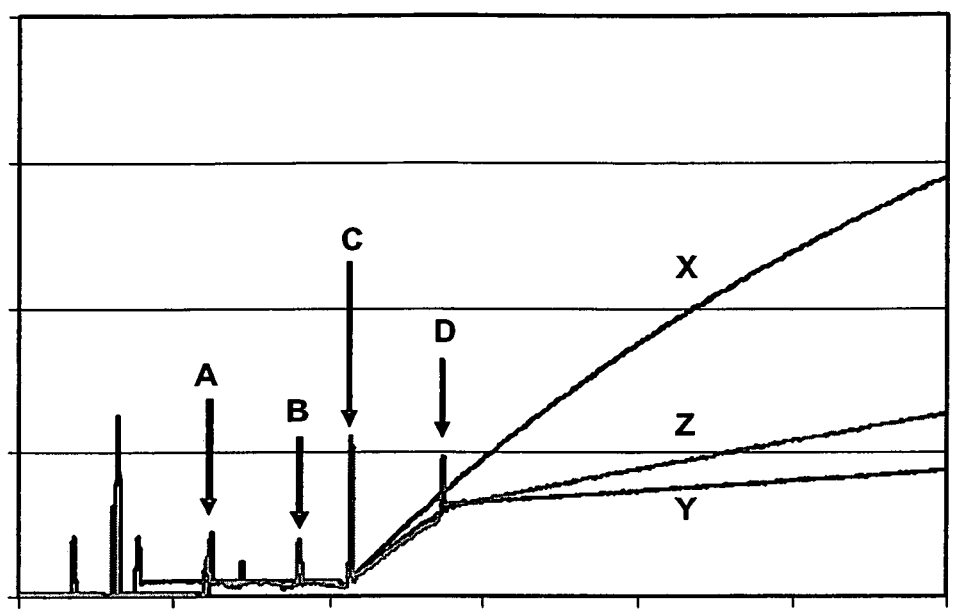

Upon calcium activation, the rate of cleavage of the FRET substrate by m-calpain (FIG. 1A) was approximately four times higher than that catalyzed by (FIG. 1B). In the absence of either inhibitor, the autolytic inactivation of m-calpain caused the fluorescence intensity to plateau after just a few minutes of reaction. However, this autolytic inactivation was not observed with Upon addition of either inhibitor, the increase in fluorescence was immediately attenuated, albeit more noticeably with m-calpain. For both m-calpain and μI-II, Z-Leu-Abu-CONH—(CH$_2$)$_3$-adenin-9-yl, caused a more distinct attenuation of fluorescence when compared to Z-Leu-Abu-CONH—(CH$_2$)$_3$-(4-methylpiperazin-1-yl), indicating that the former is a more potent calpain inhibitor. See FIG. 1.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

J is selected from the group consisting of halogen, OH, CN, NO$_2$, NH$_2$, COOH, CO$_2$Me, CO$_2$Et, CF$_3$, C$_{1-6}$ alkyl, C$_{1-4}$ alkoxy, and C$_{1-4}$ perfluoroalkyl;

AA$^2$ is a residue of an amino acid with the L configuration, D configuration, or DL configuration at the α-carbon selected from the group consisting of alanine, valine, leucine, isoleucine, proline, histidine, methionine, methionine sulfoxide, phenylalanine, serine, threonine, phenylglycine, norleucine, norvaline, alpha-aminobutyric acid, O-methylserine, O-ethylserine, S-methylcysteine, S-ethylcysteine, S-benzylcysteine, NH$_2$—CH(CH$_2$CHEt$_2$)-COOH, alpha-aminoheptanoic acid, NH$_2$—CH(CH$_2$-cyclohexyl)-COOH, NH$_2$—CH(CH$_2$-cyclopentyl)-COOH, NH$_2$—CH(CH$_2$-cyclobutyl)-COOH, NH$_2$—CH(CH$_2$-cyclopropyl)-COOH, 5,5,5-trifluoroleucine, α-aminohexanoic acid, thiaproline, and hexafluoroleucine;

What is claimed is:

1. A compound comprising the formula M-AA$^2$-AA$^1$-CO—NH—(CH$_2$)$_n$—R$^3$ or a pharmaceutically acceptable salt thereof, wherein M is selected from the group consisting of NH$_2$—CO—, NH$_2$—SO$_2$—, NH$_2$—CS, Y-FG,

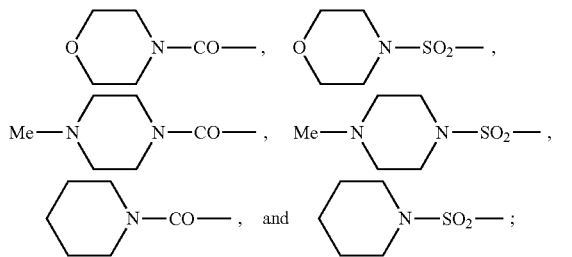

FG is selected from the group consisting of —CO—, —O—CO—, —NH—CO—, —SO$_2$—, —NH—SO$_2$—, and —NH—CS;

Y is selected from the group consisting of C$_{1-8}$ alkyl, C$_{3-15}$ cycloalkyl, C$_{1-4}$ alkyl monosubstituted with phenyl, C$_{1-4}$ alkyl disubstituted with phenyl, C$_{1-4}$ alkyl monosubstituted with Ar, C$_{1-4}$ alkyl monosubstituted with 1-naphthyl, C$_{1-4}$ alkyl monosubstituted with 2-naphthyl, and Ar;

wherein Ar is selected from the group consisting of phenyl, phenyl monosubstituted with J, phenyl disubstituted with J, 1-naphthyl, 1-naphthyl monosubstituted with J, 2-naphthyl, 2-naphthyl monosubstituted with J, 2-pyridyl, 3-pyridyl, and 4-pyridyl;

AA$^1$ is a residue of glycine or a residue of an amino acid with the L configuration, D configuration, or DL configuration at the α-carbon selected from the group consisting of alanine, valine, leucine, isoleucine, proline, histidine, methionine, methionine sulfoxide, phenylalanine, arginine, lysine, tryptophan, serine, threonine, cysteine, tyrosine, asparagine, glutamine, aspartic acid, glutamic acid, phenylglycine, norleucine, norvaline, alpha-aminobutyric acid, O-methylserine, O-ethylserine, S-methylcysteine, S-ethylcysteine, S-benzylcysteine, NH$_2$—CH(CH$_2$CHEt$_2$)—COOH, alpha-aminoheptanoic acid, NH$_2$—CH(CH$_2$-1-naphthyl)-COOH, NH$_2$—CH(CH$_2$-2-naphthyl)-COOH, NH$_2$—CH(CH$_2$-cyclohexyl)-COOH, NH$_2$—CH(CH$_2$-cyclopentyl)-COOH, NH$_2$—CH(CH$_2$-cyclobutyl)-COOH, NH$_2$—CH(CH$_2$-cyclopropyl)-COOH, 5,5,5-trifluoroleucine, homophenylalanine, hexafluoroleucine, α-aminohexanoic acid, phenylalanine monosubstituted on the phenyl group with K, and homophenylalanine monosubstituted on the phenyl group with K;

K is selected from the group consisting of halogen, C$_{1-6}$ alkyl, and C$_{1-4}$ alkoxy;

n=1-5;

R$^3$ is selected from the group consisting of

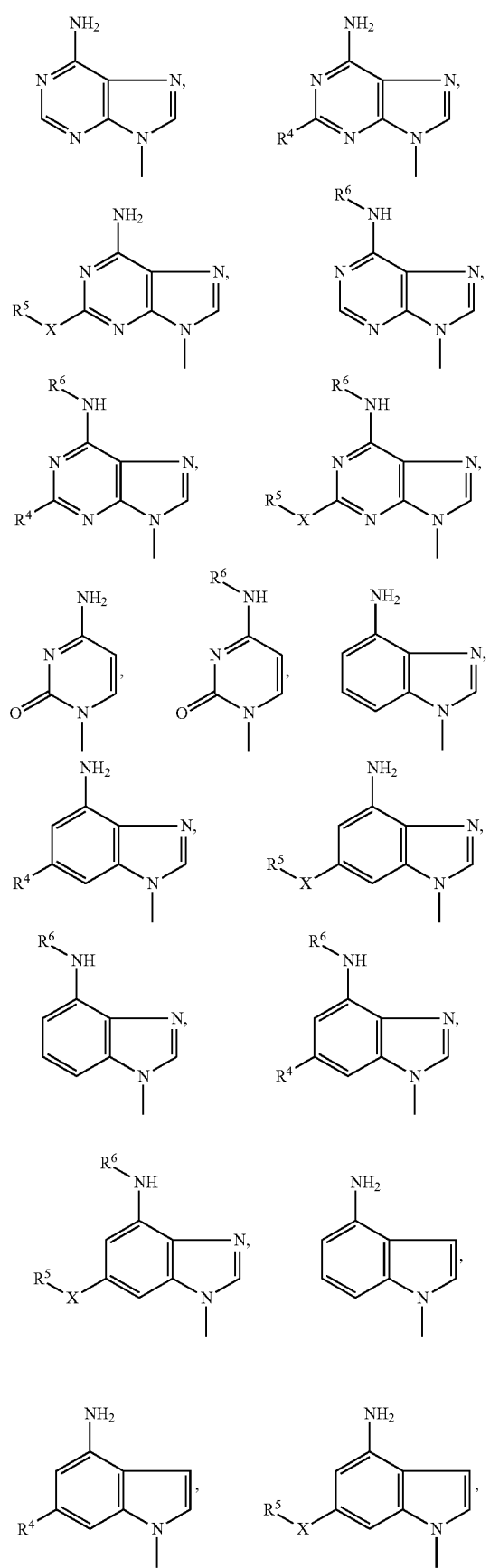
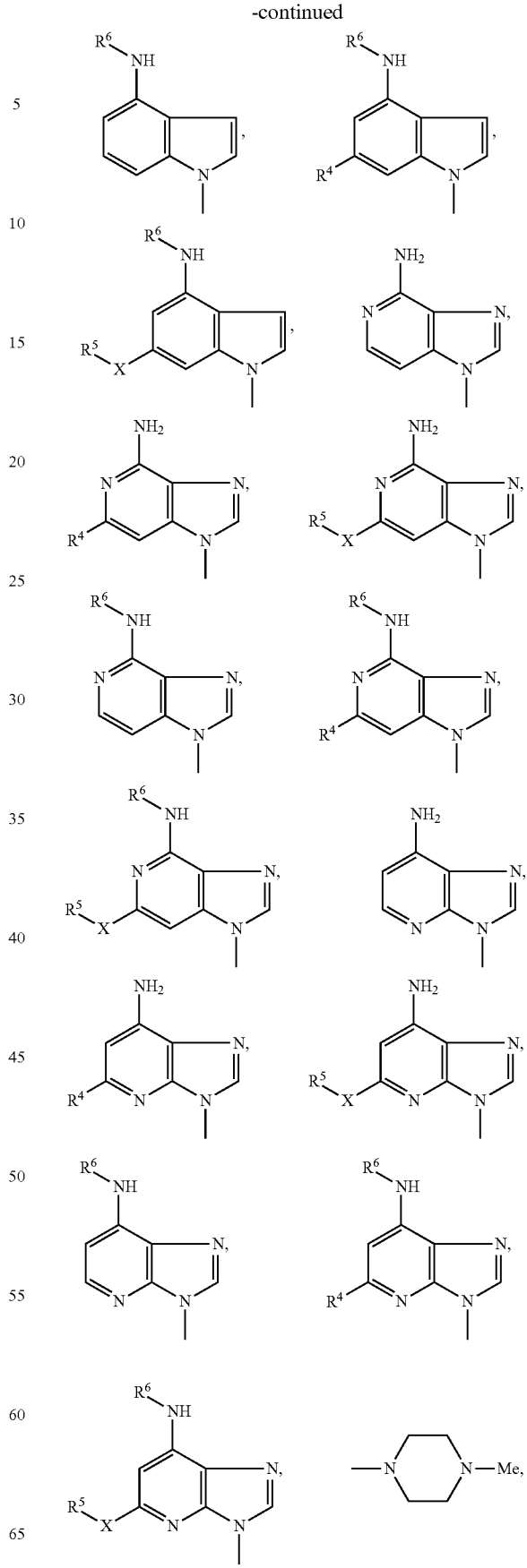

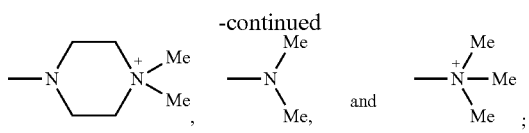

X is selected from O, NH, and S;

$R^4$ is selected from the group consisting of $C_{1-6}$ alkyl, phenyl, and benzyl;

$R^5$ is selected from the group consisting of $C_{1-6}$ alkyl, phenyl, and benzyl; and $R^6$ is selected from the group consisting of $C_{1-6}$ alkyl, phenyl, and benzyl.

2. The compound of claim 1, or a pharmaceutically acceptable salt thereof, wherein $R^3$ is selected from the group consisting of

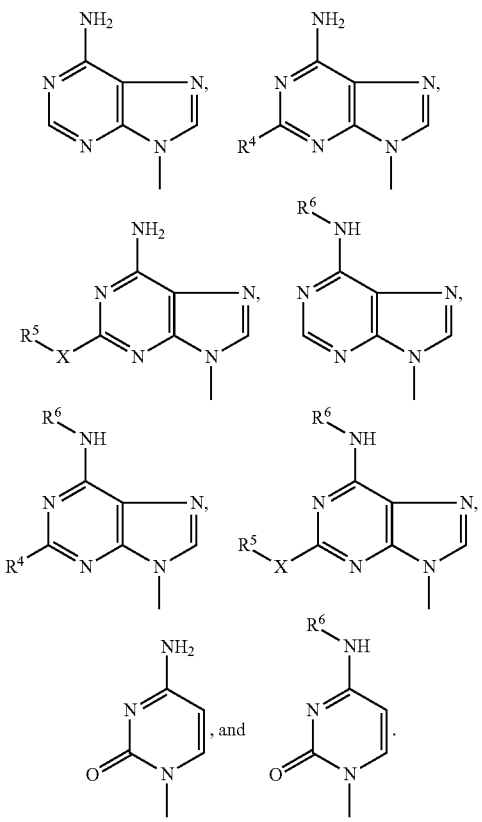

3. The compound of claim 2, or a pharmaceutically acceptable salt thereof, wherein FG is selected from the group consisting of —CO—, —O—CO—, and —NH—CO—;

$AA^2$ is a residue of an amino acid with the L configuration, D configuration, or DL configuration at the α-carbon selected from the group consisting of alanine, valine, leucine, isoleucine, proline, histidine, methionine, methionine sulfoxide, phenylalanine, serine, threonine, phenylglycine, norleucine, norvaline, alpha-aminobutyric acid, O-methylserine, O-ethylserine, S-methylcysteine, S-ethylcysteine, S-benzylcysteine, and alpha-aminoheptanoic acid; and $AA^1$ is a residue of glycine or a residue of an amino acid with the L configuration, D configuration, or DL configuration at the α-carbon selected from the group consisting of alanine, valine, leucine, isoleucine, proline, histidine, methionine, methionine sulfoxide, phenylalanine, arginine, lysine, tryptophan, serine, threonine, cysteine, tyrosine, asparagine, glutamine, aspartic acid, glutamic acid, phenylglycine, norleucine, norvaline, alpha-aminobutyric acid, O-methylserine, O-ethylserine, S-methylcysteine, S-ethylcysteine, S-benzylcysteine, alpha-aminoheptanoic acid, NH$_2$—CH(CH$_2$-1-naphthyl)-COOH, NH$_2$—CH(CH$_2$-2-naphthyl)-COOH, homophenylalanine, hexafluoroleucine, and α-aminohexanoic acid.

4. The compound of claim 3, or a pharmaceutically acceptable salt thereof, wherein $R^4$ is selected from the group consisting of $C_{1-6}$ alkyl; $R^5$ is selected from the group consisting of $C_{1-6}$ alkyl; and $R^6$ is selected from the group consisting of $C_{1-6}$ alkyl.

5. The compound of claim 1, or a pharmaceutically acceptable salt thereof, wherein $R^3$ is

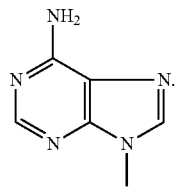

6. The compound of claim 5, or a pharmaceutically acceptable salt thereof, wherein FG is selected from the group consisting of —CO—, —O—CO—, and —NH—CO—;

$AA^2$ is a residue of an amino acid with the L configuration, D configuration, or DL configuration at the α-carbon selected from the group consisting of alanine, valine, leucine, isoleucine, proline, histidine, methionine, methionine sulfoxide, phenylalanine, serine, threonine, phenylglycine, norleucine, norvaline, alpha-aminobutyric acid, O-methylserine, O-ethylserine, S-methylcysteine, S-ethylcysteine, S-benzylcysteine, and alpha-aminoheptanoic acid; and $AA^1$ is a residue of glycine or a residue of an amino acid with the L configuration, D configuration, or DL configuration at the α-carbon selected from the group consisting of alanine, valine, leucine, isoleucine, proline, histidine, methionine, methionine sulfoxide, phenylalanine, arginine, lysine, tryptophan, glycine, serine, threonine, cysteine, tyrosine, asparagine, glutamine, aspartic acid, glutamic acid, phenylglycine, norleucine, norvaline, alpha-aminobutyric acid, O-methylserine, O-ethylserine, S-methylcysteine, S-ethylcysteine, S-benzylcysteine, alpha-aminoheptanoic acid, NH$_2$—CH(CH$_2$-1-naphthyl)-COOH, NH$_2$—CH(CH$_2$-2-naphthyl)-COOH, homophenylalanine, hexafluoroleucine, and α-aminohexanoic acid.

7. The compound of claim 6, or a pharmaceutically acceptable salt thereof, wherein FG is selected from the group consisting of —O—CO— and —NH—CO—.

8. The compound of claim 1, or a pharmaceutically acceptable salt thereof, wherein $R^3$ is selected from the group consisting of

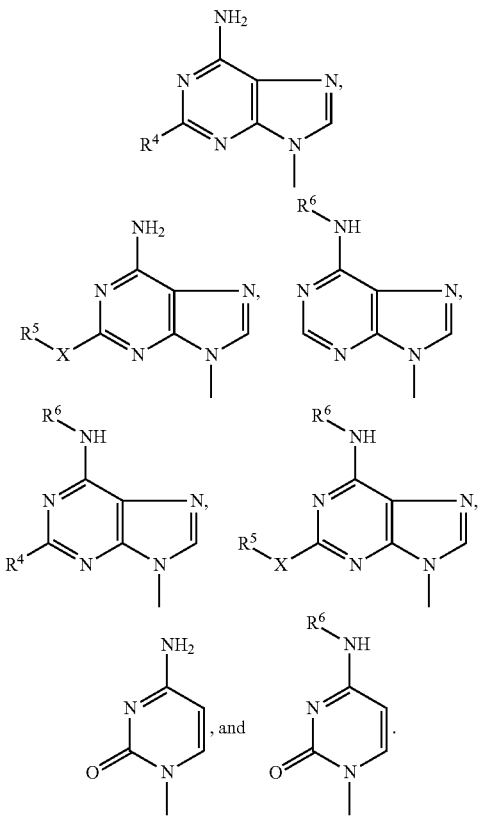

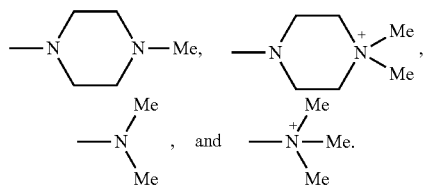

9. The compound of claim 8, or a pharmaceutically acceptable salt thereof, wherein FG is selected from the group consisting of —CO—, —O—CO—, and —NH—CO—;

AA² is a residue of an amino acid with the L configuration, D configuration, or DL configuration at the α-carbon selected from the group consisting of alanine, valine, leucine, isoleucine, proline, histidine, methionine, methionine sulfoxide, phenylalanine, serine, threonine, phenylglycine, norleucine, norvaline, alpha-aminobutyric acid, O-methylserine, O-ethylserine, S-methylcysteine, S-ethylcysteine, S-benzylcysteine, and alpha-aminoheptanoic acid; and AA¹ is a residue of glycine or a residue of an amino acid with the L configuration, D configuration, or DL configuration at the α-carbon selected from the group consisting of alanine, valine, leucine, isoleucine, proline, histidine, methionine, methionine sulfoxide, phenylalanine, arginine, lysine, tryptophan, serine, threonine, cysteine, tyrosine, asparagine, glutamine, aspartic acid, glutamic acid, phenylglycine, norleucine, norvaline, alpha-aminobutyric acid, O-methylserine, O-ethylserine, S-methylcysteine, S-ethylcysteine, S-benzylcysteine, alpha-aminoheptanoic acid, $NH_2$—$CH(CH_2$-1-naphthyl)-COOH, $NH_2$—$CH(CH_2$-2-naphthyl)-COOH, homophenylalanine, hexafluoroleucine, and α-aminohexanoic acid.

10. The compound of claim 9, or a pharmaceutically acceptable salt thereof, wherein $R^4$ is $C_{1-6}$ alkyl; $R^5$ is $C_{1-6}$ alkyl; and $R^6$ is $C_{1-6}$ alkyl.

11. The compound of claim 1, or a pharmaceutically acceptable salt thereof, wherein $R^3$ is selected from the group consisting of 12. The compound of claim 11, or a pharmaceutically acceptable salt thereof, wherein FG is selected from the group consisting of —CO—, —O—CO—, and —NH—CO—;

AA² is a residue of an amino acid with the L configuration, D configuration, or DL configuration at the α-carbon selected from the group consisting of alanine, valine, leucine, isoleucine, proline, histidine, methionine, methionine sulfoxide, phenylalanine, serine, threonine, phenylglycine, norleucine, norvaline, alpha-aminobutyric acid, O-methylserine, O-ethylserine, S-methylcysteine, S-ethylcysteine, S-benzylcysteine, and alpha-aminoheptanoic acid; and AA¹ is a residue of glycine or a residue of an amino acid with the L configuration, D configuration, or DL configuration at the α-carbon selected from the group consisting of alanine, valine, leucine, isoleucine, proline, histidine, methionine, methionine sulfoxide, phenylalanine, arginine, lysine, tryptophan, serine, threonine, cysteine, tyrosine, asparagine, glutamine, aspartic acid, glutamic acid, phenylglycine, norleucine, norvaline, alpha-aminobutyric acid, O-methylserine, O-ethylserine, S-methylcysteine, S-ethylcysteine, S-benzylcysteine, alpha-aminoheptanoic acid, $NH_2$—$CH(CH_2$-1-naphthyl)-COOH, $NH_2$—$CH(CH_2$-2-naphthyl)-COOH, homophenylalanine, hexafluoroleucine, and α-aminohexanoic acid.

13. The compound of claim 12, or a pharmaceutically acceptable salt thereof, wherein $R^4$ is $C_{1-6}$ alkyl; $R^5$ is $C_{1-6}$ alkyl; and $R^6$ is $C_{1-6}$ alkyl.

14. A compound, or a pharmaceutically acceptable salt thereof, selected from the group consisting of
Z-Leu-Abu-CONH—$(CH_2)_3$-adenin-9-yl,
Z-Leu-Phe-CONH—$(CH_2)_3$-adenin-9-yl,
Z-Leu-Hph-CONH—$(CH_2)_3$-adenin-9-yl,
Z-Val-Abu-CONH—$(CH_2)_3$-adenin-9-yl,
Z-Val-Phe-CONH—$(CH_2)_3$-adenin-9-yl,
Z-Val-Hph-CONH—$(CH_2)_3$-adenin-9-yl,
Z-Leu-Abu-CONH—$(CH_2)_3$-2-methyladenin-9-yl,
Z-Leu-Phe-CONH—$(CH_2)_3$-2-methyladenin-9-yl,
Z-Leu-Hph-CONH—$(CH_2)_3$-2-methyladenin-9-yl,
Z-Val-Abu-CONH—$(CH_2)_3$-2-methyladenin-9-yl,
Z-Val-Phe-CONH—$(CH_2)_3$-2-methyladenin-9-yl,
Z-Val-Hph-CONH—$(CH_2)_3$-2-methyladenin-9-yl,
Z-Leu-Abu-CONH—$(CH_2)_3$-2-methoxyadenin-9-yl,
Z-Leu-Phe-CONH—$(CH_2)_3$-2-methoxyadenin-9-yl,
Z-Leu-Hph-CONH—$(CH_2)_3$-2-methoxyadenin-9-yl,
Z-Val-Abu-CONH—$(CH_2)_3$-2-methoxyadenin-9-yl,
Z-Val-Phe-CONH—$(CH_2)_3$-2-methoxyadenin-9-yl,
Z-Val-Hph-CONH—$(CH_2)_3$-2-methoxyadenin-9-yl,
Z-Leu-Abu-CONH—$(CH_2)_3$-cytosin-3-yl,
Z-Leu-Phe-CONH—$(CH_2)_3$-cytosin-3-yl,
Z-Leu-Hph-CONH—$(CH_2)_3$-cytosin-3-yl,
Z-Val-Abu-CONH—$(CH_2)_3$-cytosin-3-yl,
Z-Val-Phe-CONH—$(CH_2)_3$-cytosin-3-yl,
Z-Val-Hph-CONH—$(CH_2)_3$-cytosin-3-yl,
Z-Leu-Abu-CONH—$(CH_2)_3$-(4-methylpiperazin-1-yl),
Z-Leu-Phe-CONH—$(CH_2)_3$-(4-methylpiperazin-1-yl), Z-Leu-Hph-CONH—(CH$_2$)$_3$-(4-methylpiperazin-1-yl),
Z-Val-Abu-CONH—(CH$_2$)$_3$-(4-methylpiperazin-1-yl),
Z-Val-Phe-CONH—(CH$_2$)$_3$-(4-methylpiperazin-1-yl),
Z-Val-Hph-CONH—(CH$_2$)$_3$-(4-methylpiperazin-1-yl),
Z-Leu-Abu-CONH—(CH$_2$)$_3$—N(CH$_3$)$_2$,
Z-Leu-Phe-CONH—(CH$_2$)$_3$—N(CH$_3$)$_2$,
Z-Leu-Hph-CONH—(CH$_2$)$_3$—N(CH$_3$)$_2$,
Z-Val-Abu-CONH—(CH$_2$)$_3$—N(CH$_3$)$_2$,
Z-Val-Phe-CONH—(CH$_2$)$_3$—N(CH$_3$)$_2$,
Z-Val-Hph-CONH—(CH$_2$)$_3$—N(CH$_3$)$_2$,
Z-Leu-Abu-CONH—(CH$_2$)$_2$—N(CH$_3$)$_2$,
Z-Leu-Phe-CONH—(CH$_2$)$_2$—N(CH$_3$)$_2$,
Z-Leu-Hph-CONH—(CH$_2$)$_2$—N(CH$_3$)$_2$,
Z-Val-Abu-CONH—(CH$_2$)$_2$—N(CH$_3$)$_2$,
Z-Val-Phe-CONH—(CH$_2$)$_2$—N(CH$_3$)$_2$,
Z-Val-Hph-CONH—(CH$_2$)$_2$—N(CH$_3$)$_2$,
Mu-Leu-Abu-CONH—(CH$_2$)$_3$-adenin-9-yl,
Mu-Leu-Phe-CONH—(CH$_2$)$_3$-adenin-9-yl,
Mu-Leu-Hph-CONH—(CH$_2$)$_3$-adenin-9-yl,
Mu-Val-Abu-CONH—(CH$_2$)$_3$-adenin-9-yl,
Mu-Val-Phe-CONH—(CH$_2$)$_3$-adenin-9-yl,
Mu-Val-Hph-CONH—(CH$_2$)$_3$-adenin-9-yl,
Mu-Leu-Abu-CONH—(CH$_2$)$_3$-2-methyladenin-9-yl,
Mu-Leu-Phe-CONH—(CH$_2$)$_3$-2-methyladenin-9-yl,
Mu-Leu-Hph-CONH—(CH$_2$)$_3$-2-methyladenin-9-yl,
Mu-Val-Abu-CONH—(CH$_2$)$_3$-2-methyladenin-9-yl,
Mu-Val-Phe-CONH—(CH$_2$)$_3$-2-methyladenin-9-yl,
Mu-Val-Hph-CONH—(CH$_2$)$_3$-2-methyladenin-9-yl,
Mu-Leu-Abu-CONH—(CH$_2$)$_3$-2-methoxyadenin-9-yl,
Mu-Leu-Phe-CONH—(CH$_2$)$_3$-2-methoxyadenin-9-yl,
Mu-Leu-Hph-CONH—(CH$_2$)$_3$-2-methoxyadenin-9-yl,
Mu-Val-Abu-CONH—(CH$_2$)$_3$-2-methoxyadenin-9-yl,
Mu-Val-Phe-CONH—(CH$_2$)$_3$-2-methoxyadenin-9-yl,
Mu-Val-Hph-CONH—(CH$_2$)$_3$-2-methoxyadenin-9-yl,
Mu-Leu-Abu-CONH—(CH$_2$)$_3$-cytosin-3-yl,
Mu-Leu-Phe-CONH—(CH$_2$)$_3$-cytosin-3-yl,
Mu-Leu-Hph-CONH—(CH$_2$)$_3$-cytosin-3-yl,
Mu-Val-Abu-CONH—(CH$_2$)$_3$-cytosin-3-yl,
Mu-Val-Phe-CONH—(CH$_2$)$_3$-cytosin-3-yl,
Mu-Val-Hph-CONH—(CH$_2$)$_3$-cytosin-3-yl,
Mu-Leu-Abu-CONH—(CH$_2$)$_3$-(4-methylpiperazin-1-yl),
Mu-Leu-Phe-CONH—(CH$_2$)$_3$-(4-methylpiperazin-1-yl),
Mu-Leu-Hph-CONH—(CH$_2$)$_3$-(4-methylpiperazin-1-yl),
Mu-Val-Abu-CONH—(CH$_2$)$_3$-(4-methylpiperazin-1-yl),
Mu-Val-Phe-CONH—(CH$_2$)$_3$-(4-methylpiperazin-1-yl),
Mu-Val-Hph-CONH—(CH$_2$)$_3$-(4-methylpiperazin-1-yl),
Mu-Leu-Abu-CONH—(CH$_2$)$_3$—N(CH$_3$)$_2$,
Mu-Leu-Phe-CONH—(CH$_2$)$_3$—N(CH$_3$)$_2$,
Mu-Leu-Hph-CONH—(CH$_2$)$_3$—N(CH$_3$)$_2$,
Mu-Val-Abu-CONH—(CH$_2$)$_3$—N(CH$_3$)$_2$,
Mu-Val-Phe-CONH—(CH$_2$)$_3$—N(CH$_3$)$_2$,
Mu-Val-Hph-CONH—(CH$_2$)$_3$—N(CH$_3$)$_2$,
Mu-Leu-Abu-CONH—(CH$_2$)$_2$—N(CH$_3$)$_2$,
Mu-Leu-Phe-CONH—(CH$_2$)$_2$—N(CH$_3$)$_2$,
Mu-Leu-Hph-CONH—(CH$_2$)$_2$—N(CH$_3$)$_2$,
Mu-Val-Abu-CONH—(CH$_2$)$_2$—N(CH$_3$)$_2$,
Mu-Val-Phe-CONH—(CH$_2$)$_2$—N(CH$_3$)$_2$,
Mu-Val-Hph-CONH—(CH$_2$)$_2$—N(CH$_3$)$_2$,
Pip-CO-Leu-Abu-CONH—(CH$_2$)$_3$-adenin-9-yl,
Pip-CO-Leu-Phe-CONH—(CH$_2$)$_3$-adenin-9-yl,
Pip-CO-Leu-Hph-CONH—(CH$_2$)$_3$-adenin-9-yl,
Pip-CO-Val-Abu-CONH—(CH$_2$)$_3$-adenin-9-yl,
Pip-CO-Val-Phe-CONH—(CH$_2$)$_3$-adenin-9-yl,
Pip-CO-Val-Hph-CONH—(CH$_2$)$_3$-adenin-9-yl,
Pip-CO-Leu-Abu-CONH—(CH$_2$)$_3$-2-methyladenin-9-yl,
Pip-CO-Leu-Phe-CONH—(CH$_2$)$_3$-2-methyladenin-9-yl,
Pip-CO-Leu-Hph-CONH—(CH$_2$)$_3$-2-methyladenin-9-yl,
Pip-CO-Val-Abu-CONH—(CH$_2$)$_3$-2-methyladenin-9-yl,
Pip-CO-Val-Phe-CONH—(CH$_2$)$_3$-2-methyladenin-9-yl,
Pip-CO-Val-Hph-CONH—(CH$_2$)$_3$-2-methyladenin-9-yl,
Pip-CO-Leu-Abu-CONH—(CH$_2$)$_3$-2-methoxyadenin-9-yl,
Pip-CO-Leu-Phe-CONH—(CH$_2$)$_3$-2-methoxyadenin-9-yl,
Pip-CO-Leu-Hph-CONH—(CH$_2$)$_3$-2-methoxyadenin-9-yl,
Pip-CO-Val-Abu-CONH—(CH$_2$)$_3$-2-methoxyadenin-9-yl,
Pip-CO-Val-Phe-CONH—(CH$_2$)$_3$-2-methoxyadenin-9-yl,
Pip-CO-Val-Hph-CONH—(CH$_2$)$_3$-2-methoxyadenin-9-yl,
Pip-CO-Leu-Abu-CONH—(CH$_2$)$_3$-cytosin-3-yl,
Pip-CO-Leu-Phe-CONH—(CH$_2$)$_3$-cytosin-3-yl,
Pip-CO-Leu-Hph-CONH—(CH$_2$)$_3$-cytosin-3-yl,
Pip-CO-Val-Abu-CONH—(CH$_2$)$_3$-cytosin-3-yl,
Pip-CO-Val-Phe-CONH—(CH$_2$)$_3$-cytosin-3-yl,
Pip-CO-Val-Hph-CONH—(CH$_2$)$_3$-cytosin-3-yl,
Pip-CO-Leu-Abu-CONH—(CH$_2$)$_3$-(4-methylpiperazin-1-yl),
Pip-CO-Leu-Phe-CONH—(CH$_2$)$_3$-(4-methylpiperazin-1-yl),
Pip-CO-Leu-Hph-CONH—(CH$_2$)$_3$-(4-methylpiperazin-1-yl),
Pip-CO-Val-Abu-CONH—(CH$_2$)$_3$-(4-methylpiperazin-1-yl),
Pip-CO-Val-Phe-CONH—(CH$_2$)$_3$-(4-methylpiperazin-1-yl),
Pip-CO-Val-Hph-CONH—(CH$_2$)$_3$-(4-methylpiperazin-1-yl),
Pip-CO-Leu-Abu-CONH—(CH$_2$)$_3$—N(CH$_3$)$_2$,
Pip-CO-Leu-Phe-CONH—(CH$_2$)$_3$—N(CH$_3$)$_2$,
Pip-CO-Leu-Hph-CONH—(CH$_2$)$_3$—N(CH$_3$)$_2$,
Pip-CO-Val-Abu-CONH—(CH$_2$)$_3$—N(CH$_3$)$_2$,
Pip-CO-Val-Phe-CONH—(CH$_2$)$_3$—N(CH$_3$)$_2$,
Pip-CO-Val-Hph-CONH—(CH$_2$)$_3$—N(CH$_3$)$_2$,
Pip-CO-Leu-Abu-CONH—(CH$_2$)$_2$—N(CH$_3$)$_2$,
Pip-CO-Leu-Phe-CONH—(CH$_2$)$_2$—N(CH$_3$)$_2$,
Pip-CO-Leu-Hph-CONH—(CH$_2$)$_2$—N(CH$_3$)$_2$,
Pip-CO-Val-Abu-CONH—(CH$_2$)$_2$—N(CH$_3$)$_2$,
Pip-CO-Val-Phe-CONH—(CH$_2$)$_2$—N(CH$_3$)$_2$,
Pip-CO-Val-Hph-CONH—(CH$_2$)$_2$—N(CH$_3$)$_2$,
PhPr-Leu-Abu-CONH—(CH$_2$)$_3$-adenin-9-yl,
PhPr-Leu-Phe-CONH—(CH$_2$)$_3$-adenin-9-yl,
PhPr-Leu-Hph-CONH—(CH$_2$)$_3$-adenin-9-yl,
PhPr-Val-Abu-CONH—(CH$_2$)$_3$-adenin-9-yl,
PhPr-Val-Phe-CONH—(CH$_2$)$_3$-adenin-9-yl,
PhPr-Val-Hph-CONH—(CH$_2$)$_3$-adenin-9-yl,
PhPr-Leu-Abu-CONH—(CH$_2$)$_3$-2-methyladenin-9-yl,
PhPr-Leu-Phe-CONH—(CH$_2$)$_3$-2-methyladenin-9-yl,
PhPr-Leu-Hph-CONH—(CH$_2$)$_3$-2-methyladenin-9-yl,
PhPr-Val-Abu-CONH—(CH$_2$)$_3$-2-methyladenin-9-yl,
PhPr-Val-Phe-CONH—(CH$_2$)$_3$-2-methyladenin-9-yl,
PhPr-Val-Hph-CONH—(CH$_2$)$_3$-2-methyladenin-9-yl,
PhPr-Leu-Abu-CONH—(CH$_2$)$_3$-2-methoxyadenin-9-yl,
PhPr-Leu-Phe-CONH—(CH$_2$)$_3$-2-methoxyadenin-9-yl,
PhPr-Leu-Hph-CONH—(CH$_2$)$_3$-2-methoxyadenin-9-yl,
PhPr-Val-Abu-CONH—(CH$_2$)$_3$-2-methoxyadenin-9-yl,
PhPr-Val-Phe-CONH—(CH$_2$)$_3$-2-methoxyadenin-9-yl,
PhPr-Val-Hph-CONH—(CH$_2$)$_3$-2-methoxyadenin-9-yl,
PhPr-Leu-Abu-CONH—(CH$_2$)$_3$-cytosin-3-yl,
PhPr-Leu-Phe-CONH—(CH$_2$)$_3$-cytosin-3-yl,
PhPr-Leu-Hph-CONH—(CH$_2$)$_3$-cytosin-3-yl,
PhPr-Val-Abu-CONH—(CH$_2$)$_3$-cytosin-3-yl, PhPr-Val-Phe-CONH—(CH$_2$)$_3$-cytosin-3-yl,
PhPr-Val-Hph-CONH—(CH$_2$)$_3$-cytosin-3-yl,
PhPr-Leu-Abu-CONH—(CH$_2$)$_3$-4-methylpiperazin-1-yl),
PhPr-Leu-Phe-CONH—(CH$_2$)$_3$-(4-methylpiperazin-1-yl),
PhPr-Leu-Hph-CONH—(CH$_2$)$_3$-(4-methylpiperazin-1-yl),
PhPr-Val-Abu-CONH—(CH$_2$)$_3$-(4-methylpiperazin-1-yl),
PhPr-Val-Phe-CONH—(CH$_2$)$_3$-(4-methylpiperazin-1-yl),
PhPr-Val-Hph-CONH—(CH$_2$)$_3$-(4-methylpiperazin-1-yl),
PhPr-Leu-Abu-CONH—(CH$_2$)$_3$—N(CH$_3$)$_2$,
PhPr-Leu-Phe-CONH—(CH$_2$)$_3$—N(CH$_3$)$_2$,
PhPr-Leu-Hph-CONH—(CH$_2$)$_3$—N(CH$_3$)$_2$,
PhPr-Val-Abu-CONH—(CH$_2$)$_3$—N(CH$_3$)$_2$,
PhPr-Val-Phe-CONH—(CH$_2$)$_3$—N(CH$_3$)$_2$,
PhPr-Val-Hph-CONH—(CH$_2$)$_3$—N(CH$_3$)$_2$,
PhPr-Leu-Abu-CONH—(CH$_2$)$_2$—N(CH$_3$)$_2$,
PhPr-Leu-Phe-CONH—(CH$_2$)$_2$—N(CH$_3$)$_2$,
PhPr-Leu-Hph-CONH—(CH$_2$)$_2$—N(CH$_3$)$_2$,
PhPr-Val-Abu-CONH—(CH$_2$)$_2$—N(CH$_3$)$_2$,
PhPr-Val-Phe-CONH—(CH$_2$)$_2$—N(CH$_3$)$_2$, and
PhPr-Val-Hph-CONH—(CH$_2$)$_2$—N(CH$_3$)$_2$.

15. The compound of claim 1, wherein said compound substantially comprises a single optical isomer.

16. A pharmaceutical composition comprising an effective amount of a compound of claim 1, and a pharmaceutically acceptable carrier.

17. A method of inhibiting a cysteine protease, comprising: contacting the cysteine protease with a compound of claim 1.

18. The method of claim 17, wherein the contacting occurs in vivo.

19. The method of claim 17, wherein the contacting occurs in vitro.

20. The method of claim 17, wherein the cysteine protease comprises a calpain.

21. The method of claim 17, wherein the cysteine protease comprises a member of the clan CA of cysteine proteases.

22. A method of treating a neurodegenerative disorder, comprising:
administering an effective amount of a compound of claim 1 to a host having a neurodegenerative disorder or symptoms thereof.

23. The method of claim 22, wherein the neurodegenerative disorder is selected from the group consisting of stroke, Alzheimer's disease, Parkinson's disease, multiple sclerosis, neuropathies, Huntington's disease, dentatorubropallidoluysian atrophy, spinocerebellar atrophy type 3, spinal bulbar muscular atrophy, and myotrophic lateral sclerosis.

24. A method of treatment of nerve degeneration due to diabetes or a neurotoxic agent, comprising: administering to a patient a therapeutically effective amount of a compound of claim 1.

* * * * *

SEQUENCE LISTING

<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Glu Pro Leu Phe Ala Glu Arg Lys
1               5